United States Patent
West et al.

(10) Patent No.: US 9,938,641 B2
(45) Date of Patent: Apr. 10, 2018

(54) SELECTION OF APTAMERS BASED ON GEOMETRY

(75) Inventors: Jason Andrew Appleton West, Pleasanton, CA (US); Brent Coleman Satterfield, Mesa, AZ (US)

(73) Assignee: FLUIDIGM CORPORATION, South San Francisco, CA (US)

( * ) Notice: Subject to any disclaimer, the term of this patent is extended or adjusted under 35 U.S.C. 154(b) by 1300 days.

(21) Appl. No.: 11/959,435

(22) Filed: Dec. 18, 2007

(65) Prior Publication Data

US 2008/0182759 A1 Jul. 31, 2008

Related U.S. Application Data

(60) Provisional application No. 60/870,493, filed on Dec. 18, 2006.

(51) Int. Cl.
| | | |
|---|---|---|
| C40B 20/00 | (2006.01) | |
| C40B 30/04 | (2006.01) | |
| C40B 20/08 | (2006.01) | |
| C12N 15/115 | (2010.01) | |
| C40B 40/08 | (2006.01) | |

(52) U.S. Cl.
CPC ......... *C40B 20/08* (2013.01); *C12N 15/115* (2013.01); *C40B 30/04* (2013.01); *C40B 40/08* (2013.01); *C07B 2200/11* (2013.01); *C12N 2310/16* (2013.01); *C12N 2320/10* (2013.01)

(58) Field of Classification Search
USPC ..... 424/9.1; 435/6.1, 6.12, 91.1, 455, 91.31, 435/458; 514/44; 536/23.1, 24.5; 506/9
See application file for complete search history.

(56) References Cited

U.S. PATENT DOCUMENTS

| | | | |
|---|---|---|---|
| 4,469,863 A | 9/1984 | Ts'o et al. |
| 4,486,539 A | 12/1984 | Ranki et al. |
| 4,563,419 A | 1/1986 | Ranki et al. |
| 4,683,195 A | 7/1987 | Mullis et al. |
| 4,711,955 A | 12/1987 | Ward et al. |
| 4,731,325 A | 3/1988 | Palva et al. |
| 4,988,617 A | 1/1991 | Landegren et al. |
| 4,996,143 A | 2/1991 | Heller et al. |
| 5,034,506 A | 7/1991 | Summerton et al. |
| 5,066,584 A | 11/1991 | Gyllensten et al. |
| 5,075,216 A | 12/1991 | Innis et al. |
| 5,091,310 A | 2/1992 | Innis |
| 5,118,801 A | 6/1992 | Lizardi et al. |
| 5,142,033 A | 8/1992 | Innis |
| 5,210,015 A | 5/1993 | Gelfand et al. |
| 5,216,141 A | 6/1993 | Benner |
| 5,219,727 A | 6/1993 | Wang et al. |
| 5,235,033 A | 8/1993 | Summerton et al. |
| 5,310,652 A | 5/1994 | Gelfand et al. |
| 5,312,728 A | 5/1994 | Lizardi et al. |
| 5,314,809 A | 5/1994 | Erlich et al. |
| 5,322,770 A | 6/1994 | Gelfand |
| 5,386,023 A | 1/1995 | Sanghvi et al. |
| 5,389,512 A | 2/1995 | Kwok et al. |
| 5,391,480 A | 2/1995 | Davis et al. |
| 5,407,800 A | 4/1995 | Gelfand et al. |
| 5,411,876 A | 5/1995 | Bloch et al. |
| 5,418,149 A | 5/1995 | Gelfand et al. |
| 5,445,935 A | 8/1995 | Royer |
| 5,468,613 A | 11/1995 | Erlich et al. |
| 5,476,774 A | 12/1995 | Wang et al. |
| 5,487,972 A | 1/1996 | Gelfand et al. |
| 5,512,462 A | 4/1996 | Cheng |
| 5,525,494 A | 6/1996 | Newton |
| 5,538,848 A | 7/1996 | Livak et al. |
| 5,539,082 A | 7/1996 | Nielsen et al. |
| 5,561,058 A | 10/1996 | Gelfand et al. |
| 5,565,339 A | 10/1996 | Bloch et al. |
| 5,573,906 A | 11/1996 | Bannwarth et al. |
| 5,585,481 A | 12/1996 | Arnold, Jr. et al. |
| 5,593,840 A | 1/1997 | Bhatnagar et al. |
| 5,595,890 A | 1/1997 | Newton et al. |
| 5,602,240 A | 2/1997 | De Mesmaeker et al. |
| 5,604,099 A | 2/1997 | Erlich et al. |
| 5,607,834 A | 3/1997 | Bagwell |
| 5,618,703 A | 4/1997 | Gelfand et al. |
| 5,637,684 A | 6/1997 | Cook et al. |
| 5,641,864 A | 6/1997 | Gelfand |
| 5,644,048 A | 7/1997 | Yau |
| 5,693,517 A | 12/1997 | Gelfand et al. |
| 5,723,591 A | 3/1998 | Livak et al. |
| 5,728,526 A | 3/1998 | George, Jr. et al. |
| 5,770,365 A | 6/1998 | Lane et al. |
| 5,773,571 A | 6/1998 | Nielsen et al. |
| 5,801,055 A | 9/1998 | Henderson |
| 5,804,375 A | 9/1998 | Gelfand et al. |
| 5,866,336 A | 2/1999 | Nazarenko et al. |
| 5,876,930 A | 3/1999 | Livak et al. |
| 5,925,517 A | 7/1999 | Tyagi et al. |
| 5,977,296 A | 11/1999 | Nielson et al. |
| 5,989,817 A | 11/1999 | Söderlund et al. |
| 5,994,056 A | 11/1999 | Higuchi |
| 5,994,076 A | 11/1999 | Chenchik et al. |
| 6,001,611 A | 12/1999 | Will |
| 6,007,984 A | 12/1999 | Wang et al. |

(Continued)

FOREIGN PATENT DOCUMENTS

| | | |
|---|---|---|
| WO | WO 93/13121 A1 | 7/1993 |
| WO | WO 95/32305 A1 | 11/1995 |

(Continued)

OTHER PUBLICATIONS

Stratis-Cullum et al. (Development of nucleic acid aptamer-based sensors for the direct detection and identification of biological agents, (2003) Proceedings of the Joint Service Scientific Conference on Chemical and Biological Defense Research, Towson MD Nov. 17-20, 2003, Report date Oct. 2005).*

(Continued)

*Primary Examiner* — Jane Zara
(74) *Attorney, Agent, or Firm* — Emily M. Haliday; Weaver Austin Villeneuve & Sampson LLP

(57) ABSTRACT

Disclosed are methods for performing aptamer preselection based on unique geometry and the content of stems or loops of the aptamer, which methods are capable of providing suitable binders and also permit selection of aptamers performed essentially entirely on a chip or other device. Also disclosed are kits for aptamer selection.

61 Claims, 8 Drawing Sheets

(56) References Cited

U.S. PATENT DOCUMENTS

| | | | |
|---|---|---|---|
| 6,022,686 | A | 2/2000 | Garman et al. |
| 6,030,787 | A | 2/2000 | Livak et al. |
| 6,037,130 | A | 3/2000 | Tyagi et al. |
| 6,040,166 | A | 3/2000 | Erlich et al. |
| 6,090,552 | A | 7/2000 | Nazarenko et al. |
| 6,103,476 | A | 8/2000 | Tyagi et al. |
| 6,117,635 | A | 9/2000 | Nazarenko et al. |
| 6,127,121 | A | 10/2000 | Meyer, Jr. et al. |
| 6,140,055 | A | 10/2000 | Todd et al. |
| 6,150,097 | A | 11/2000 | Tyagi et al. |
| 6,171,785 | B1 | 1/2001 | Higuchi |
| 6,197,563 | B1 | 3/2001 | Erlich et al. |
| 6,201,113 | B1 | 3/2001 | Todd et al. |
| 6,214,979 | B1 | 4/2001 | Gelfand et al. |
| 6,251,588 | B1 | 6/2001 | Shannon et al. |
| 6,258,569 | B1 | 7/2001 | Livak et al. |
| 6,270,967 | B1 | 8/2001 | Whitcombe et al. |
| 6,326,145 | B1 | 12/2001 | Whitcombe et al. |
| 6,350,580 | B1 | 2/2002 | Sorge |
| 6,361,941 | B1 | 3/2002 | Todd et al. |
| 6,365,724 | B2 | 4/2002 | Todd et al. |
| 6,426,408 | B1 | 7/2002 | Kutyavin et al. |
| 6,432,642 | B1 | 8/2002 | Livak et al. |
| 6,461,817 | B1 | 10/2002 | Alland et al. |
| 6,511,810 | B2 | 1/2003 | Bi et al. |
| 6,589,743 | B2 | 7/2003 | Sorge |
| 6,649,349 | B2 | 11/2003 | Gildea et al. |
| 6,713,262 | B2 | 3/2004 | Gellibolian et al. |
| 6,716,583 | B2 | 4/2004 | Gold et al. |
| 6,730,478 | B1 | 5/2004 | Lee et al. |
| 6,821,727 | B1 | 11/2004 | Livak et al. |
| 6,861,222 | B2 | 3/2005 | Ward et al. |
| 6,949,367 | B1 | 9/2005 | Dempcy et al. |
| 6,962,906 | B2 | 11/2005 | Efimov et al. |
| 6,972,328 | B2 | 12/2005 | Gall et al. |
| 7,057,025 | B2 | 6/2006 | Livak et al. |
| 7,070,933 | B2 | 7/2006 | Browne |
| 7,192,710 | B2 | 3/2007 | Gellibolian et al. |
| 7,230,092 | B2 | 6/2007 | Bortolin et al. |
| 2003/0105320 | A1 | 6/2003 | Becker et al. |
| 2003/0235828 | A1 | 12/2003 | Gillibolian et al. |
| 2004/0091864 | A1 | 5/2004 | French et al. |
| 2005/0158720 | A1 | 7/2005 | Li et al. |
| 2007/0118296 | A1* | 5/2007 | SantaLucia ............ G06F 19/16 702/20 |

FOREIGN PATENT DOCUMENTS

| | | |
|---|---|---|
| WO | WO 95/32306 A1 | 11/1995 |
| WO | WO 00/29617 A2 | 5/2000 |
| WO | WO 01/42505 A2 | 6/2001 |
| WO | WO 01/86001 A1 | 11/2001 |
| WO | WO 01/94625 A2 | 12/2001 |
| WO | WO 2004/081520 A2 | 9/2004 |
| WO | WO 2006/002547 A1 | 1/2006 |
| WO | WO 2007/114986 A2 | 10/2007 |

OTHER PUBLICATIONS

Apte et al. (PCR primer design, in PCR Primer: a Laboratory Manual, Eds. Dieffenbach and Dveksler, 2003, pp. 61, 70-74, and cover pages, 8 pages total.*

Collett et al. (Production and processing of aptamer microarrays, 2005, Methods, vol. 37, pp. 4-15).*

Asai et al. (In vitro selection of DNA aptamers on chips using a method for generating point mutations, 2004, Analytical Letters, vol. 37, pp. 645-656, provided by applicants in IDS).*

Bruno et al. (In vitro selection of DNA aptamers to anthrax spores with electrochemiluminescence detection, 1999, Biosensors and Bioelectronics, vol. 14, pp. 457-464).*

Tsang et al. (Evolutionary optimization of the catalytic properties of a DNA-cleaving ribozyme, 1994, Biochemistry, vol. 33, pp. 5966-5973).*

Wang et al. (Single-stranded DNA aptamers that bind differentiated but not parental cells: subtractive systematic evolution of ligands by exponential enrichment, 2003, Journal of Biotechnology, vol. 102, pp. 15-22, provided by applicants in IDS).*

Gevertz et al. (In vitro RNA random pools are not structurally diverse: a computational analysis, 2005, Bioinformatics, vol. 11, pp. 853-863).*

Smirnov et al. (Effect of loop sequence and size on DNA aptamer stability, 2000, Biochemistry, vol. 39, pp. 1462-1468).*

Gevertz et al, Bioinformatics, vol. 11, pp. 853-863 (2005).*

Asai et al, Analytical Letters, vol. 37, pp. 645-656 (2004).*

Wang et al, J. of Biotechnology, vol. 102, pp. 15-22 (2003).*

Tsang et al, Biochemistry, vol. 33, pp. 5966-5973 (1994).*

Asai, R et al. (2004) "In Vitro Selection of DNA Aptamers on Chips Using a Method for Generating Point Mutations". Chemical and Biosensors, 37, 645-656.

Bates et al. "Cooperativity of paired oligonucleotide probes for microarray hybridization assays", (2005) Anal. Biochem. 342(1):59-68.

Bhanot et al. "The importance of thermodynamic equilibrium for high throughput gene expression arrays," (2003) Biophys J. 84(1):124-135.

Bollum et al. "Oligodeoxyribonucleotide-primed reactions catalyzed by calf thymus polymerase," J. Biol. Chem. 237(6): 1945-1949.

Call (2005) "Challenges and opportunities for pathogen detection using DNA microarrays," Crit. Rev. Microbiol. 31(2):91-99.

Caplan and Rosca "Targeting drugs to combinations of receptors: a modeling analysis of potential specificity," (2005) Ann. Biomed. Eng. 33(8):1113-1124.

Carlsson et al. "Screening for genetic mutations," (1996) Nature 380:207.

Cerchia, L. et al (2005) "Neutralizing aptamers from whole-cell SELEX inhibit the RET receptor tyrosine kinase," PLoS Biol, 3, e123, pp. 0697-0704.

Chase et al. "Real-time PCR assays targeting a unique chromosomal sequence of Yersinia pestis," Clin. Chem, 51, (2005) 1778-1785.

Chen and Dovichi (1994) "Yoctomole detection limit by laser-induced fluorescence in capillary electrophoresis," J. Chromatogr. B Biomed. Appl. 657(2):265-269.

Christensen et al. "Additivity and the physical basis of multivalency effects: a thermodynamic investigation of the calcium EDTA interaction," (2003) J. Am. Chem. Soc., 125(24): 7357-7366.

Compton, "Nucleic acid sequence-based amplification," 1991, Nature 350:91-92.

Crothers et al. "The influence of polyvalency on the binding properties of antibodies ," (1972) Immunochemistry, 9(3):341-357.

D'Aquila et al. "Maximizing sensitivity and specificity of PCR by pre-amplification heating," (1991) Nucleic Acids Res. 19:3749.

Dai et al. "Use of hybridization kinetics for differentiating specific from non-specific binding to oligonucleotide microarrays," (2002) Nucleic Acids Res. 30(16):e86.

Dang, C. and Jayasena, S.D. (1996) "Oligonucleotide inhibitors of Taq DNA polymerase facilitate detection of low copy number targets by PCR,". J Mol Biol, 264, 268-278.

Daniels, D.A., et al. (2002) "Generation of RNA aptamers to the G-protein-coupled receptor for neurotensin, NTS-1," Anal Biochem, 305, 214-226.

De Mesmaeker et al., "Comparison of Rigid and Flexible Backbones in Antisense Oligonucleotides," (1994), Bioorganic & Medicinal Chem. Lett. 4:395-398.

De Mesmaeker, A. et al., "Novel Backbone Replacements for Oligonucleotides," Ch. 2 in ASC Symposium Series 580, Carbohydrate Modifications in Antisense Research, Ed. Y. S. Sanghui and P. Dan Cook, 1994, 24-39.

Dempcy et al. "Synthesis of a thymidyl pentamer of deoxyribonucleic guanidine and binding studies with DNA homopolynucleotides," (1995) Proc. Natl. Acad. Sci. USA 92:6097-6101.

Dmitriev et al. "Kinetic analysis of interactions between bispecific monoclonal antibodies and immobilized antigens using a resonant mirror biosensor," (2003) J. Immunol. Methods, 280(1-2):183-202.

(56) References Cited

OTHER PUBLICATIONS

Dmitriev et al. (2002) "Analysis of the binding of bispecific monoclonal antibodies with immobilized antigens (human IgG and horseradish peroxidase) using a resonant mirror biosensor," J. Immunol. Methods, 261(1-2):103-118.

Drake and Tan "Molecular beacon DNA probes and their bioanalytical applications," (2004) Appl. Spectrosc. 58(9):269A-280A.

Egholm, M. et al., "Peptide Nucleic Acids (PNA). Oligonucleotide Analogues with an Achiral Peptide Backbone," (1992) J. Am. Chem. Soc. 114:1895-1897.

Fan and Merritt "Combating infectious diseases through multivalent design," (2002) Curr. Drug Targets Infect. Disord. 2(2):161-167.

Frommer et al. "A genomic sequencing protocol that yields a positive display of 5-methylcytosine residues in individual DNA strands," (1992) Proc. Natl. Acad. Sci. U.S.A. 89: 1827-1831.

Gonzalez et al. "Race-specific HIV-1 disease-modifying effects associated with CCR5 haplotypes," (1999) Proc. Natl. Acad. Sci. U.S.A. 96(21):12004-12009.

Hamaguchi et al. "Aptamer beacons for the direct detection of proteins," (2001) Anal. Biochem. 294(2):126-131.

Hirao, I. et al. (2000) "RNA aptamers that bind to and inhibit the ribosome-inactivating protein, pepocin," J Biol Chem, 275, 4943-4948.

Holland et al. "Detection of specific polymerase chain reaction product by utilizing the 5'-3' exonuclease activity of Thermus aquaticus DNA polymerase," (1991) Proc. Natl Acad Sci. U.S.A. 88:7276-7280.

Horn, T. et al. "Oligonucleotides with Alternating Anionic and Cationic Phosphoramidate Linkages: Synthesis and Hybridization of Stereo-uniform Isomers," (1996) Tetrahedron Lett. 37(6):743-746.

Hubble "A model of multivalent ligand-receptor equilibria which explains the effect of multivalent binding inhibitors," (1999) Mol. Immunol. 36(1):13-18.

Hurtle et al "Detection of the Bacillus anthracis gyrA gene by using a minor groove binder probe," (J. Clin Microbiol, 42, (2004) 179-185.

Huskens et al. "A model for describing the thermodynamics of multivalent host-guest interactions at interfaces," (2004) J. Am. Chem. Soc. 126(21):6784-6797.

Gao et al. "Unusual conformation of a 3'-thioformacetal linkage in a DNA duplex," (1994) J Biomolecular NMR, 34:17-34.

Jencks "On the attribution and additivity of binding energies," (1981) Proc. Natl. Acad. Sci. U.S.A., 78(7):4046-4050.

Jenkins et al. "The Biosynthesis of Carbocyclic Nucleosides," (1995), Chem. Soc. Rev. pp. 169-176.

Kaufman et al., "Effect of Bivalent Interaction upon Apparent Antibody Affinity: Experimental Confirmation of Theory Using Fluorescence Photobleaching and Implications for Antibody Binding Assays," (1992) Cancer Res., 52(15):4157-4167.

Kiedrowski et al. "Parabolic Growth of a Self-Replicating Hexadeoxynucleotide Bearing a 3'-5'-Phosphoamidate Linkage," (1991) Angew. Chem. Intl. Ed. English 30:423-426.

Kiessling et al. "Synthetic multivalent ligands in the exploration of cell-surface interactions," (2000) Curr. Opin. Chem. Biol. 4(6):696-703.

Kitov and Bundle "On the nature of the multivalency effect: a thermodynamic model," (2003) J. Am. Chem. Soc. 125(52):16271-16284.

Kuske et al. "Small-Scale DNA Sample Preparation Method for Field PCR Detection of Microbial Cells and Spores in Soil," (2002) Appl. Environ. Microbiol. 64(7):2463-2472.

Lee et al. "Guidelines for incorporating non-perfectly matched oligonucleotides into target-specific hybridization probes for a DNA microarray," (2004) Nucleic Acids Res. 32(2):681-690.

Lee et al. "New energy transfer dyes for DNA sequencing," (1997) Nucleic Acids Res. 25:2816-2822.

Letowski et al., "Designing better probes: effect of probe size, mismatch position and number on hybridization in DNA oligonucleotide microarrays," (2004)J. Microbiol. Methods, 57(2):269-278.

Letsinger "Phosphoramidate analogs of oligonucleotides," (1970)1 Org. Chem. 35:3800-3803.

Letsinger et al. "Effects of pendant groups at phosphorus on binding properties of d-ApA analogues," (1986) Nucleic Acids Res. 14:3487-3499.

Jung et al., "Hybridization of Alternating Cationic/Anionic Oligonucleotides to RNA Segments," (1994) Nucleoside & Nucleotide 13:1597-1605.

Letsinger, R.L. et al. "Cationic Oligonucleotides," (1988) J. Am. Chem. Soc. 110:4470-4471.

Li and Tan (2003) "A real-time assay for DNA sticky-end pairing using molecular beacons," Anal. Biochem. 312(2):251-254.

Li et al. "Molecular aptamer beacons for real-time protein recognition," (2002) Biochem. Biophys. Res. Commun. 292(1):31-40.

Li et al. "Using molecular beacons as a sensitive fluorescence assay for enzymatic cleavage of single-stranded DNA," (2000) Nucleic Acids Res. 28(11):E52.

Liu et al. "Optimization of an oligonucleotide microchip for microbial identification studies: a non-equilibrium dissociation approach," (2001) Environ. Micro biol. 3(10): 619-629.

Lizardi, P.M. et al. "Exponential Amplication of Recombinant-RNA Hybridization Probes," 1988, Bio/Technology 6, 1197-1202.

Loge et al. "PCR detection of specific pathogens in water: a risk-based analysis," (2002) Environ. Sci. Technol. 36(12):2754-2759.

Maddry, J.A. et al., "Synthesis of Nonionic Oligonucleotide Analogues," Ch. 3 in ASC Symposium Series 580, Carbohydrate Modifications in Antisense Research, Ed. Y. S. Sanghui and P. Dan Cook, 1994, 40-51.

Mag et al. "Synthesis and selective cleavage of an oligodeoxynucleotide containing a bridged internucleotide 5'-phosphorothioate linkage ," (1991) Nucleic Acids Res. 19:1437.

Mammen et al., "Polyvalent Interactions in Biological Systems: Implications for Design and Use of Multivalent Ligands and Inhibitors," (1998) Angew. Chem. Int. Ed. 37(20):2754-2794.

Mannironi, C. et al. (1997) "In vitro selection of dopamine RNA ligands," Biochemistry, 36, 9726-9734.

Marras et al. "Efficiencies of fluorescence resonance energy transfer and contact-mediated quenching in oligonucleotide probes," (2002) Nucleic Acids Res. 30(21):e122, pp. 1-8.

Marras et al. "Real-time assays with molecular beacons and other fluorescent nucleic acid hybridization probes," (2006) Clin. Chim. Acta 363(1-2):48-60.

Matsuo, "In situ visualization of messenger RNA for basic fibroblast growth factor in living cells," (1988) Biochim. Biophys. Acta 1379(2):178-184.

Matthews et al. "Analytical strategies for the use of DNA probes ," (1988) Analyt. Biochem. 169:1-25.

Meier et al. "Peptide Nucleic Acids (PNAs)—Unusual Properties of Nonionic Oligonucleotide Analogues," (1992) Chem. Mt. Ed. Engl. 31:1008-1010.

Mendonsa, S.D. and Bowser, M.T. (2004) "In vitro evolution of functional DNA using capillary electrophoresis," J Am Chem Soc, 126, 20-21.

Mendonsa, S.D. and Bowser, M.T. (2005) "In vitro selection of aptamers with affinity for neuropeptide Y using capillary electrophoresis," J Am Chem Soc, 127, 9382-9383.

Mescalchin, A. et al (2006) "Specific binding of a hexanucleotide to HIV-1 reverse transcriptase: a novel class of bioactive molecules," Nucleic Acids Res., 34(19), 5631-5637.

Muller et al. "Model and simulation of multivalent binding to fixed ligands ," (1998) Anal. Biochem. 261(2):149-158.

Egholm et al "PNA hybridizes to the complementary oligonucleotides obeying Watson-Crick hydrogen-bonding rules," (1993) Nature 365:566-568.

Nyholm, L., "Electrochemical techniques for lab-on-a-chip applications," (2005) Analyst 130(5):599-605.

Okazawa, A. (2000) "In vitro selection of hematoporphyrin binding DNA aptamers," Bioorg Med Chem Lett, 10, 2653-2656.

Pauwels et al., "Biological Activity of New 2-5 A Analogues," (1986) Chemica Scripta 26:141-145.

(56) References Cited

OTHER PUBLICATIONS

Peplies et al. "Optimization strategies for DNA microarray-based detection of bacteria with 16S rRNA-targeting oligonucleotide probes," (2003) Appl. Environ. Microbiol. 69(3):1397-1407.
Perelson et al. "Optimal strategies in immunology III. The IgM-IgG switch," (1980) J. Math. Biol., 10(3):209-256.
Perelson, "Some mathematical models of receptor clustering by multivalent ligands," in Cell Surface Dynamics: Concepts and Models, Perelson, A.S., et al. Ed., New York, Marcel Dekker, 223-276 (1984).
Perlette "Real-time monitoring of intracellular mRNA hybridization inside single living cells ," (2001) Anal. Chem. 73(22):5544-5550.
Pileur, F. et al. (2003) "Selective inhibitory DNA aptamers of the human RNase H1," Nucleic Acids Res, 31, 5776-5788.
Ramachandran et al. "Target discrimination by surface-immobilized molecular beacons designed to detect Francisella tularensis ," (2004) Biosens. Bioelectron. 19(7):727-736.
Relogio et al. "Optimization of oligonucleotide-based DNA microarrays," (2002) Nucleic Acids Res. 30(11):e51.
Rhodes, A. et al. (2000) "The generation and characterization of antagonist RNA aptamers to human oncostatin M," J Biol Chem, 275, 28555-28561.
Ruckman, J. et al. 1998) "2'-Fluoropyrimidine RNA-based aptamers to the 165-amino acid form of vascular endothelial growth factor (VEGF165). Inhibition of receptor binding and VEGF-induced vascular permeability through interactions requiring the exon 7-encoded domain," J Biol Chem, 273, 20556-20567.
Sawai et al. "Synthesis and Properties of Oligoadenylic Acids Containing 2'-5' Phosphoramide Linkage," (1984) Chem. Lett., 13(5), 805-808.
Schneider, D. et al. (1993) "Selective enrichment of RNA species for tight binding to *Escherichia coli* rho factor," Faseb J, 7, 201-207.
Sprinzl et al. "Enzymatic incorporation of ATP and CTP analogues into the 3' end of tRNA ," (1977) Eur. J. Biochem. 81:579-589.
Sproat et al. "The synthesis of protected 5'-amino-2',5'-dideoxyribonucleoside-3'-O-phosphoramidites; applications of 5'-amino-oligodeoxyribonucleotides," (1987) Nucleic Acids Res. 15:6181-6196.
Surugiu-Warnmark, I. et al. (2005) "Selection of DNA aptamers against rat liver X receptors," Biochem Biophys Res Commun, 332, 512-517.
Tang et al. "Real-time monitoring of nucleic acid ligation in homogenous solutions using molecular beacons," (2003) Nucleic Acids Res. 31(23):e148, pp. 1-7.
Tasset, D.M. et al. (1997) "Oligonucleotide inhibitors of human thrombin that bind distinct epitopes," J Mol Biol, 272, 688-698.
Tombelli et al. "Analytical applications of aptamers ," (2005) Biosens. Bioelectron. 20(12):2424-2434.
Tsourkas Andrew et al., "Hybridization kinetics and thermodynamics of molecular beacons." Nucleic Acids Research, vol. 31, No. 4, Feb. 15, 2003 (Feb. 15, 2003), pp. 1319-1330, XP002455592.
Tsourkas et al. "Hybridization kinetics and thermodynamics of molecular beacons," (2003) Nucleic Acids Res. 31(4).1319-1330.
Tsuji et al. "Direct observation of specific messenger RNA in a single living cell under a fluorescence microscope," (2000) Biophys. J. 78(6):3260-3274.
Tu, et al. "3'-end labeling of DNA with [alpha-32P]cordycepin-5'-triphosphate ," (1980) Gene 10:177-183.
Tuerk, C. and Gold, L. (1990) Systematic evolution of ligands by exponential enrichment: RNA ligands to bacteriophage T4 DNA polymerase. Science, 249, 505-510.
Tyagi and Kramer "Molecular beacons: probes that fluoresce upon hybridization," 1996 Nat. Biotechnol. 14(3):303-308.
Vo, N.V. et al. (2003) "Identification of RNA ligands that bind hepatitis C virus polymerase selectively and inhibit its RNA synthesis from the natural viral RNA templates," Virology, 307, 301-316.
Walker et al., "Isothermal in vitro amplification of DNA by a restriction enzyme/DNA polymerase system," 1992, Proc. Natl. Acad. Sci. U.S.A. 89:392 396.

Wang, C. et al. (2003) "Single-stranded DNA aptamers that bind differentiated but not parental cells: subtractive systematic evolution of ligands by exponential enrichment," J Biotechnol, 102, 15-22.
Yamamoto et al. "Molecular beacon aptamer fluoresces in the presence of Tat protein of HIV-1," (2000) Genes Cells 5(5):389-396.
Yang, Q., Goldstein, I.J., Mei, H.Y. and Engelke, D.R. (1998) "DNA ligands that bind tightly and selectively to cellobiose," Proc Natl Acad Sci U S A, 95, 5462-5467.
Yao and Tan "Molecular-beacon-based array for sensitive DNA analysis," 2004 Anal. Biochem. 331(2):216-223.
Zarrin "Sub-Picoliter Detection with the Sheath Flow Cuvette," (1985) Analytical chemistry 57(13):2690-2692.
Draghici et al. "Applications and challenges of DNA microarray technology in military medical research," (2004) Mil. Med. 169(8):654-659.
Drake and Tan "Molecular beacon DNA probes and their bioanalytical applications," (2004) Appl. Spectrosc, 58(9):269A-280A.
Egholm, M. et al.. "Peptide Nucleic Acids (PNA). Oligonucleotide Analogues with an Achiral Peptide Backbone," (1992) J. Am. Chem. Soc. 114:1895-1897.
Ellington and Szostak, "In vitro selection of RNA molecules that bind specific ligands," Nature 346:818-822 (1990).
Fan and Merritt "Combating infectious diseases through multivalent design," (2002) Curr. Drug Targets Infect. Disord. 2(2):161-187.
Frommer et al. "A genomic sequencing protocol that yields a positive display of 5-methylcytosine residues in individual DNA strands," (1992) Proc. Natl. Acad. Sci. U.S.A. 89:1827-1831.
Gentalen and Chee "A novel method for determining linkage between DNA sequences: hybridization to paired probe arrays," (1999) Nucleic Acids Res. 27(6):1485-14.
Gonzalez et al. "Race-specific HIV-1 disease-modifying effects associated with CCR5 haplotypes," (1999) Proc. Natl. Aced, Sci. U.S.A. 96(21):12004-12009.
Guatelli et al. "Isothermal, in vitro amplification of nucleic acids by a multienzyme reaction modeled after retroviral replication," 1990, Proc. Nat. Acad. Sci. USA 87, 1874-1878.
Halperin et al. "Sensitivity, specificity, and the hybridization isotherms of DNA chips," (2004) Biophys. J. 86(2):718-730.
Hamaguchi et al. "Aptamer beacons for the direct detection of proteins," (2001) Anal. Biochem. 294(2):126-131.
Handl et al. "Hitting multiple targets with multimeric ligands," (2004) Expert Open. Ther. Targets 8(6):565-586.
Herdewijn, P. et al., "Hexopyranosyl-Like Oligonucleotides," Ch. 6 in ASC Symposium Series 580, Carbohydrate Modifications in Antisense Research, Ed. Y. S. Sanghui and P. Dan Cook, 1994, 80-99.
Hirao, I, et al, (2000) "RNA aptamers that bind to and inhibit the ribosome-inactivating protein, pepocin," J Biol Chem, 275, 4943-4948.
Hirao, I. et al. (1998) "The limits of specificity: an experimental analysis with RNA aptamers to MS2 coat protein variants," Mol Divers, 4, 75-89.
Holland et al. "Detection of specific polymerase chain reaction product by utilizing the 5'—3' exonuclease activity of Thermus aquaticus DNA polymerase," (1991) Proc. Natl Aced Sci. U.S.A. 88:7276-7280.
Horn, T. et al. "Oligonucleotides with Alternating Anionic and Cationic Phosphoramidate Linkages: Synthesis and Hybridization of Stereo-uniform Isomers," (1996) Tetrahedron Lett. 37(6)743-746.
Amarasinghe, A.K. (2001) "An in vitro-selected RNA-binding site for the KH domain protein PSI acts as a splicing inhibitor element," RNA, 7, 1239-1253.
Asai, R et al. (2004) "In Vitro Selection of DNA Aptamers on Chips Using a Method for Generating Point Mutations", Chemical and Biosensors, 37, 645-656.
Bates et at "Cooperativity of paired oligonucleotide probes for microarray hybridization assays", (2005) Anal. Biochem. 342(1):59-68.
Beaucage et al. "The Functionalization of Oligonucleotides Via Phosphoramidite Derivatives", (1993) Tetrahedron 49(10):1925-1963.

(56) References Cited

OTHER PUBLICATIONS

Bellecave, P. et al. (2003) "Selection of DNA aptamers that bind the RNA-dependent RNA polymerase of hepatitis C virus and inhibit viral RNA synthesis in vitro" Oligonucleotides, 13, 455-463.

Bhanot et al. "The importance of thermodynamis equillibrium for high throughput gene expression arrays," (2003) Biophys J. 84(1):124-135.

Boiziau, C. et al. (1999) "DNA aptamers selected against the HIV-1 trans-activation-responsive RNA element form RNA-DNA kissing complexes," J Biol Chem, 274, 12730-12737.

Bolli, M. et al., "α-Bicyclo-DNA: Synthesis, Characterization, and Pairing Properties of α-DNA-Analogues with Restricted Conformational Flexibility in the Sugar-Phosphate Backbone," Ch. 7 in ASC Symposium Series 580, Carbohydrate Modifications in Antisense Research, Ed. Y. S. Sanghui and P. Dan Cook, 1994, 100-117.

Bolium et al, "Oligodeoxyribonucleotide-primed reactions catalyzed by calf thymus polymerase," J. Biol. Chem. 237(6): 1945-1949.

Bonnet G et al., "Thermodynamic basis of the enhanced specificity of structured DNA probes" Proceedings Of The National Academy Of Sciences Of Usa, National Academy Of Science, Washington, DC, US, vol. 96, No. 11, May 25, 1999 (May 25, 1999), pp. 6171-6176, XP002244958.

Borst et al. "False-positive results and contamination in nucleic acid amplification assays: suggestions for a prevent and destroy strategy," (2004) Eur. J. Clin. Microbiol. Infect. Dis., 2004, 23(4):289-299.

Brill et al. "Synthesis of Oligodeoxynucleoside Phosphorodithioates via Thioamidites," (1989) J. Am. Chem. Soc. 111:2321-2322.

Broude N E: "Stem-loop oligonucleotides: a robust tool for molecular biology and biotechnology" Trends in Biotechnology, Elsevier Publications, Cambridge, GB, vol. 20, No. 6, Jun. 1, 2002 (Jun. 1, 2002), pp. 249-256, XP004352763.

Call (2005) "Challenges and opportunities for pathogen detection using DNA microarrays,"Crit. Rev. Microbiol. 31(2):91-99.

\* cited by examiner

Chip Selection of Aptamers

○ Nonbinding aptamer
⊗ Aptamer specific to target
⦀ Aptamer specific to near-neighbor
⊘ Nonspecific aptamer

SEQUENCE LISTING

<160> NUMBER OF SEQ ID NOS: 326

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

```
<400> SEQUENCE: 1
gccgccgaaa aaaaaaacgg cggc                                          24

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 2
gccgcagcaa aaaaaaagcg cggc                                          24

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
gccgcgcaaa aaaaagcag cggc                                           24

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 4
gccgagccaa aaaaaaggc cggc                                           24

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 5
gccggccaaa aaaaaggca cggc                                           24

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 6
gccgaaagca aaaaaaaagc cggc                                          24

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 7
gccggcaaaa aaaaagcaaa cggc                                          24
```

-continued

```
<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 8
gccgaagcaa aaaaaagca cggc                                             24

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
gccgagcaaa aaaaagcaa cggc                                             24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
gccgccgcaa aaaaagcgg cggc                                             24

<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 11
gccgcaagca aaaaaagcg cggc                                             24

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 12
gccgcgcaaa aaaagcaag cggc                                             24

<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 13
gccgcagcaa aaaaagcag cggc                                             24

<210> SEQ ID NO 14
<211> LENGTH: 24
<212> TYPE: DNA
<213> ORGANISM: Artificial Sequence
<220> FEATURE:
<223> OTHER INFORMATION: Synthetic oligonucleotide
```

<400> SEQUENCE: 14
gccgaagcca aaaaaaggc cggc						24

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 15
gccggccaaa aaaaggcaa cggc						24

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
gccgagccaa aaaaaggca cggc						24

<210> SEQ ID NO 17
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 17
gccgaaaagc aaaaaaagc cggc						24

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 18
gccggcaaaa aaagcaaaa cggc						24

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 19
gccgaaagca aaaaaagca cggc						24

<210> SEQ ID NO 20
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 20
gccgagcaaa aaaagcaaa cggc						24

<210> SEQ ID NO 21
<211> LENGTH: 24

-continued

<212> TYPE: DNA
<213> ORGANISM: Artificial Sequence
<220> FEATURE:
<223> OTHER INFORMATION: Synthetic oligonucleotide

<400> SEQUENCE: 21
gccgaagcaa aaaaaagcaa cggc                                              24

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 22
gccgccagca aaaaaagcgg cggc                                              24

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 23
gccgccgcaa aaaagcagg cggc                                               24

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
gccgcagcca aaaaaggcg cggc                                               24

<210> SEQ ID NO 25
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 25
gccgcgccaa aaaaggcag cggc                                               24

<210> SEQ ID NO 26
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 26
gccgcaaagc aaaaaaagcg cggc                                              24

<210> SEQ ID NO 27
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 27
gccgcgcaaa aaaagcaaag cggc                                                    24

<210> SEQ ID NO 28
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 28
gccgcaagca aaaaaagcag cggc                                                    24

<210> SEQ ID NO 29
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 29
gccgcagcaa aaaagcaag cggc                                                     24

<210> SEQ ID NO 30
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 30
gccgagccga aaaaaacggc cggc                                                    24

<210> SEQ ID NO 31
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 31
gccggccgaa aaaacggca cggc                                                     24

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 32
gccgaaagcc aaaaaaaggc cggc                                                    24

<210> SEQ ID NO 33
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 33
gccggccaaa aaaggcaaa cggc                                                     24

<210> SEQ ID NO 34
<211> LENGTH: 24
<212> TYPE: DNA
<213> ORGANISM: Artificial Sequence

```
<220> FEATURE:
<223> OTHER INFORMATION: Synthetic oligonucleotide

<400> SEQUENCE: 34
gccgaagcca aaaaaggca cggc                                           24

<210> SEQ ID NO 35
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 35
gccgagccaa aaaaggcaa cggc                                           24

<210> SEQ ID NO 36
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 36
gccgaaaaag caaaaaaagc cggc                                          24

<210> SEQ ID NO 37
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 37
gccggcaaaa aaagcaaaaa cggc                                          24

<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 38
gccgaaaagc aaaaaaagca cggc                                          24

<210> SEQ ID NO 39
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 39
gccgagcaaa aaagcaaaa cggc                                           24

<210> SEQ ID NO 40
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 40
gccgaaagca aaaaagcaa cggc                                           24
```

<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 41
gccgaagcaa aaaaagcaaa cggc                                              24

<210> SEQ ID NO 42
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 42
gccgccgcca aaaaggcgg cggc                                               24

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 43
gccgccaagc aaaaaagcgg cggc                                              24

<210> SEQ ID NO 44
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 44
gccgccgcaa aaaagcaagg cggc                                              24

<210> SEQ ID NO 45
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 45
gccgccagca aaaaagcagg cggc                                              24

<210> SEQ ID NO 46
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 46
gccgcaagcc aaaaaaggcg cggc                                              24

<210> SEQ ID NO 47
<211> LENGTH: 24
<212> TYPE: DNA
<213> ORGANISM: Artificial Sequence
<220> FEATURE:
<223> OTHER INFORMATION: Synthetic oligonucleotide

```
<400> SEQUENCE: 47
gccgcgccaa aaaaggcaag cggc                                              24

<210> SEQ ID NO 48
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 48
gccgcagcca aaaaaggcag cggc                                              24

<210> SEQ ID NO 49
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 49
gccgcaaaag caaaaaagcg cggc                                              24

<210> SEQ ID NO 50
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 50
gccgcgcaaa aaagcaaaag cggc                                              24

<210> SEQ ID NO 51
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 51
gccgcaaagc aaaaaagcag cggc                                              24

<210> SEQ ID NO 52
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 52
gccgcagcaa aaagcaaag cggc                                               24

<210> SEQ ID NO 53
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 53
gccgcaagca aaaagcaag cggc                                               24

<210> SEQ ID NO 54
```

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 54
gccgaagccg aaaaaacggc cggc                                              24

<210> SEQ ID NO 55
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 55
gccggccgaa aaacggcaa cggc                                               24

<210> SEQ ID NO 56
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 56
gccgagccga aaaacggca cggc                                               24

<210> SEQ ID NO 57
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 57
gccgaaaagc caaaaaaggc cggc                                              24

<210> SEQ ID NO 58
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 58
gccggccaaa aaaggcaaaa cggc                                              24

<210> SEQ ID NO 59
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 59
gccgaaagcc aaaaaaggca cggc                                              24

<210> SEQ ID NO 60
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 60
```

```
gccgagccaa aaaaggcaaa cggc                                          24

<210> SEQ ID NO 61
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 61
gccgaagcca aaaaggcaa cggc                                           24

<210> SEQ ID NO 62
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 62
gccgaaaaag caaaaaagca cggc                                          24

<210> SEQ ID NO 63
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 63
gccgagcaaa aaagcaaaaa cggc                                          24

<210> SEQ ID NO 64
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 64
gccgaaaagc aaaaaagcaa cggc                                          24

<210> SEQ ID NO 65
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 65
gccgaagcaa aaagcaaaa cggc                                           24

<210> SEQ ID NO 66
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 66
gccgaaagca aaaagcaaa cggc                                           24

<210> SEQ ID NO 67
<211> LENGTH: 24
<212> TYPE: DNA
```

<213> ORGANISM: Artificial Sequence
<220> FEATURE:
<223> OTHER INFORMATION: Synthetic oligonucleotide

<400> SEQUENCE: 67
gccgagcagc aaaaaagcgc cggc    24

<210> SEQ ID NO 68
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 68
gccggcagca aaaagcgca cggc    24

<210> SEQ ID NO 69
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 69
gccgagcgca aaaaagcagc cggc    24

<210> SEQ ID NO 70
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 70
gccggcgcaa aaaagcagca cggc    24

<210> SEQ ID NO 71
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 71
gccgccagcc aaaaaggcgg cggc    24

<210> SEQ ID NO 72
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 72
gccgccgcca aaaggcagg cggc    24

<210> SEQ ID NO 73
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 73
gccgccaaag caaaaagcgg cggc    24

```
<210> SEQ ID NO 74
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 74
gccgccgcaa aaagcaaagg cggc                                          24

<210> SEQ ID NO 75
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 75
gccgccaagc aaaaagcagg cggc                                          24

<210> SEQ ID NO 76
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 76
gccgccagca aaagcaagg cggc                                           24

<210> SEQ ID NO 77
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 77
gccgcagccg aaaacggcg cggc                                           24

<210> SEQ ID NO 78
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 78
gccgcgccga aaacggcag cggc                                           24

<210> SEQ ID NO 79
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 79
gccgcaaagc caaaaaggcg cggc                                          24

<210> SEQ ID NO 80
<211> LENGTH: 24
<212> TYPE: DNA
<213> ORGANISM: Artificial Sequence
<220> FEATURE:
```

<223> OTHER INFORMATION: Synthetic oligonucleotide

<400> SEQUENCE: 80
gccgcgccaa aaaggcaaag cggc                                    24

<210> SEQ ID NO 81
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 81
gccgcaagcc aaaaaggcag cggc                                    24

<210> SEQ ID NO 82
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 82
gccgcagcca aaaaggcaag cggc                                    24

<210> SEQ ID NO 83
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 83
gccgcaaaaa gcaaaaagcg cggc                                    24

<210> SEQ ID NO 84
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 84
gccgcgcaaa aagcaaaaag cggc                                    24

<210> SEQ ID NO 85
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 85
gccgcaaaag caaaaagcag cggc                                    24

<210> SEQ ID NO 86
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 86
gccgcagcaa aaagcaaaag cggc                                    24

```
<210> SEQ ID NO 87
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 87
gccgcaaagc aaaaagcaag cggc                                              24

<210> SEQ ID NO 88
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 88
gccgcaagca aaagcaaag cggc                                               24

<210> SEQ ID NO 89
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 89
gccgagccgc aaaaagcggc cggc                                              24

<210> SEQ ID NO 90
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 90
gccggccgca aaagcggca cggc                                               24

<210> SEQ ID NO 91
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 91
gccgaaagcc gaaaaacggc cggc                                              24

<210> SEQ ID NO 92
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 92
gccggccgaa aacggcaaa cggc                                               24

<210> SEQ ID NO 93
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 93
gccgaagccg aaaaacggca cggc                                          24

<210> SEQ ID NO 94
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 94
gccgagccga aaacggcaa cggc                                           24

<210> SEQ ID NO 95
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 95
gccgaaaaag ccaaaaaggc cggc                                          24

<210> SEQ ID NO 96
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 96
gccggccaaa aaggcaaaaa cggc                                          24

<210> SEQ ID NO 97
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 97
gccgaaaagc caaaaaggca cggc                                          24

<210> SEQ ID NO 98
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 98
gccgagccaa aaaggcaaaa cggc                                          24

<210> SEQ ID NO 99
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 99
gccgaaagcc aaaaaggcaa cggc                                          24

<210> SEQ ID NO 100
<211> LENGTH: 24
```

```
<212> TYPE: DNA
<213> ORGANISM: Artificial Sequence
<220> FEATURE:
<223> OTHER INFORMATION: Synthetic oligonucleotide

<400> SEQUENCE: 100
gccgaagcca aaaggcaaa cggc                                            24

<210> SEQ ID NO 101
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 101
gccgaagcag caaaaagcgc cggc                                           24

<210> SEQ ID NO 102
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 102
gccggcagca aaagcgcaa cggc                                            24

<210> SEQ ID NO 103
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 103
gccgaagcgc aaaaagcagc cggc                                           24

<210> SEQ ID NO 104
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 104
gccggcgcaa aaagcagcaa cggc                                           24

<210> SEQ ID NO 105
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 105
gccgagcaag caaaaagcgc cggc                                           24

<210> SEQ ID NO 106
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 106
```
gccggcaagc aaaaagcgca cggc                                          24

<210> SEQ ID NO 107
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 107
gccgagcgca aaagcaagc cggc                                           24

<210> SEQ ID NO 108
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 108
gccggcgcaa aagcaagca cggc                                           24

<210> SEQ ID NO 109
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 109
gccgagcagc aaaaagcgca cggc                                          24

<210> SEQ ID NO 110
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 110
gccgagcgca aaaagcagca cggc                                          24

<210> SEQ ID NO 111
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 111
gccgagcagc aaaaagcagc cggc                                          24

<210> SEQ ID NO 112
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 112
gccggcagca aaagcagca cggc                                           24

<210> SEQ ID NO 113
<211> LENGTH: 24
<212> TYPE: DNA
<213> ORGANISM: Artificial Sequence

```
<220> FEATURE:
<223> OTHER INFORMATION: Synthetic oligonucleotide

<400> SEQUENCE: 113
gccgccgccg aaaacggcgg cggc                                          24

<210> SEQ ID NO 114
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 114
gccgccgaag caaaagccgg cggc                                          24

<210> SEQ ID NO 115
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 115
gccgccggca aagcaacgg cggc                                           24

<210> SEQ ID NO 116
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 116
gccgccgagc aaaagcacgg cggc                                          24

<210> SEQ ID NO 117
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 117
gccgccaagc caaaaggcgg cggc                                          24

<210> SEQ ID NO 118
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 118
gccgccgcca aaaggcaagg cggc                                          24

<210> SEQ ID NO 119
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 119
gccgccagcc aaaaggcagg cggc                                          24
```

<210> SEQ ID NO 120
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 120
gccgccaaaa gcaaaagcgg cggc                                    24

<210> SEQ ID NO 121
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 121
gccgccgcaa aagcaaaagg cggc                                    24

<210> SEQ ID NO 122
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 122
gccgccaaag caaaagcagg cggc                                    24

<210> SEQ ID NO 123
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 123
gccgccagca aaagcaaagg cggc                                    24

<210> SEQ ID NO 124
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 124
gccgccaagc aaaagcaagg cggc                                    24

<210> SEQ ID NO 125
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 125
gccgcaagcc gaaaacggcg cggc                                    24

<210> SEQ ID NO 126
<211> LENGTH: 24
<212> TYPE: DNA
<213> ORGANISM: Artificial Sequence
<220> FEATURE:
<223> OTHER INFORMATION: Synthetic oligonucleotide

```
<400> SEQUENCE: 126
gccgcgccga aaacggcaag cggc                                              24

<210> SEQ ID NO 127
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 127
gccgcagccg aaaacggcag cggc                                              24

<210> SEQ ID NO 128
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 128
gccgcaaaag ccaaaaggcg cggc                                              24

<210> SEQ ID NO 129
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 129
gccgcgccaa aaggcaaaag cggc                                              24

<210> SEQ ID NO 130
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 130
gccgcaaagc caaaaggcag cggc                                              24

<210> SEQ ID NO 131
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 131
gccgcagcca aaaggcaaag cggc                                              24

<210> SEQ ID NO 132
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 132
gccgcaagcc aaaaggcaag cggc                                              24

<210> SEQ ID NO 133
```

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 133
gccgcaaaaa gcaaaagcag cggc                                          24

<210> SEQ ID NO 134
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 134
gccgcagcaa aagcaaaaag cggc                                          24

<210> SEQ ID NO 135
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 135
gccgcaaaag caaaagcaag cggc                                          24

<210> SEQ ID NO 136
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 136
gccgcaagca aaagcaaaag cggc                                          24

<210> SEQ ID NO 137
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 137
gccgcaaagc aaaagcaaag cggc                                          24

<210> SEQ ID NO 138
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 138
gccgcagcag caaaagcgcg cggc                                          24

<210> SEQ ID NO 139
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 139
```
gccgcgcagc aaaagcgcag cggc                                          24

<210> SEQ ID NO 140
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 140
gccgcagcgc aaaagcagcg cggc                                          24

<210> SEQ ID NO 141
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 141
gccgcgcgca aagcagcag cggc                                           24

<210> SEQ ID NO 142
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 142
gccgaagccg caaaagcggc cggc                                          24

<210> SEQ ID NO 143
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 143
gccggccgca aagcggcaa cggc                                           24

<210> SEQ ID NO 144
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 144
gccgagccgc aaaagcggca cggc                                          24

<210> SEQ ID NO 145
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 145
gccgaaaagc cgaaaacggc cggc                                          24

<210> SEQ ID NO 146
<211> LENGTH: 24
<212> TYPE: DNA

```
<210> SEQ ID NO 146
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 146
gccggccgaa acggcaaaa cggc                                          24

<210> SEQ ID NO 147
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 147
gccgaaagcc gaaaacggca cggc                                          24

<210> SEQ ID NO 148
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 148
gccgagccga aaacggcaaa cggc                                          24

<210> SEQ ID NO 149
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 149
gccgaagccg aaacggcaa cggc                                           24

<210> SEQ ID NO 150
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 150
gccgaaaaag ccaaaaggca cggc                                          24

<210> SEQ ID NO 151
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 151
gccgagccaa aaggcaaaaa cggc                                          24

<210> SEQ ID NO 152
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 152
gccgaaaagc caaaaggcaa cggc                                          24
```

<210> SEQ ID NO 153
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 153
gccgaagcca aaaggcaaaa cggc                                              24

<210> SEQ ID NO 154
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 154
gccgaaagcc aaaggcaaa cggc                                               24

<210> SEQ ID NO 155
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 155
gccgagccag caaaagcggc cggc                                              24

<210> SEQ ID NO 156
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 156
gccggccagc aaaagcggca cggc                                              24

<210> SEQ ID NO 157
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 157
gccgagccgc aaaagcaggc cggc                                              24

<210> SEQ ID NO 158
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 158
gccggccgca aaagcaggca cggc                                              24

<210> SEQ ID NO 159
<211> LENGTH: 24
<212> TYPE: DNA
<213> ORGANISM: Artificial Sequence
<220> FEATURE:

<223> OTHER INFORMATION: Synthetic oligonucleotide

<400> SEQUENCE: 159
gccgaaaaag caaaagcaaa cggc                                              24

<210> SEQ ID NO 160
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 160
gccgaaagca aagcaaaaa cggc                                               24

<210> SEQ ID NO 161
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 161
gccgaaaagc aaagcaaaa cggc                                               24

<210> SEQ ID NO 162
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 162
gccgagcagc caaaaggcgc cggc                                              24

<210> SEQ ID NO 163
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 163
gccggcagcc aaaaggcgca cggc                                              24

<210> SEQ ID NO 164
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 164
gccgagcgcc aaaaggcagc cggc                                              24

<210> SEQ ID NO 165
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 165
gccggcgcca aaaggcagca cggc                                              24

```
<210> SEQ ID NO 166
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 166
gccgaaagca gcaaaagcgc cggc                                          24

<210> SEQ ID NO 167
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 167
gccggcagca aagcgcaaa cggc                                           24

<210> SEQ ID NO 168
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 168
gccgaaagcg caaaagcagc cggc                                          24

<210> SEQ ID NO 169
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 169
gccggcgcaa aagcagcaaa cggc                                          24

<210> SEQ ID NO 170
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 170
gccgagcaaa gcaaaagcgc cggc                                          24

<210> SEQ ID NO 171
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 171
gccgagcgca aagcaaagc cggc                                           24

<210> SEQ ID NO 172
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 172
gccggcaaag caaaagcgca cggc                                        24

<210> SEQ ID NO 173
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 173
gccggcgcaa agcaaagca cggc                                         24

<210> SEQ ID NO 174
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 174
gccgaagcaa gcaaaagcgc cggc                                        24

<210> SEQ ID NO 175
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 175
gccggcaagc aaaagcgcaa cggc                                        24

<210> SEQ ID NO 176
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 176
gccgaagcgc aaaagcaagc cggc                                        24

<210> SEQ ID NO 177
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 177
gccggcgcaa aagcaagcaa cggc                                        24

<210> SEQ ID NO 178
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 178
gccgaagcag caaaagcgca cggc                                        24

<210> SEQ ID NO 179
<211> LENGTH: 24
```

```
<212> TYPE: DNA
<213> ORGANISM: Artificial Sequence
<220> FEATURE:
<223> OTHER INFORMATION: Synthetic oligonucleotide

<400> SEQUENCE: 179
gccgaagcgc aaaagcagca cggc                                              24

<210> SEQ ID NO 180
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 180
gccgaagcag caaaagcagc cggc                                              24

<210> SEQ ID NO 181
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 181
gccgagcagc aaaagcgcaa cggc                                              24

<210> SEQ ID NO 182
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 182
gccgagcgca aaagcagcaa cggc                                              24

<210> SEQ ID NO 183
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 183
gccggcagca aaagcagcaa cggc                                              24

<210> SEQ ID NO 184
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 184
gccgagcaag caaaagcgca cggc                                              24

<210> SEQ ID NO 185
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 185
```
gccgagcaag caaaagcagc cggc                                          24

<210> SEQ ID NO 186
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 186
gccggcaagc aaaagcagca cggc                                          24

<210> SEQ ID NO 187
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 187
gccgagcgca aaagcaagca cggc                                          24

<210> SEQ ID NO 188
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 188
gccgagcagc aaaagcaagc cggc                                          24

<210> SEQ ID NO 189
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 189
gccggcagca aaagcaagca cggc                                          24

<210> SEQ ID NO 190
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 190
gccgagcagc aaaagcagca cggc                                          24

<210> SEQ ID NO 191
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 191
gccgccgcag caaagcgcgg cggc                                          24

<210> SEQ ID NO 192
<211> LENGTH: 24
<212> TYPE: DNA
<213> ORGANISM: Artificial Sequence

```
<220> FEATURE:
<223> OTHER INFORMATION: Synthetic oligonucleotide

<400> SEQUENCE: 192
gccgccgcgc aaagcagcgg cggc                                          24

<210> SEQ ID NO 193
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 193
gccgccgagc caaaggccgg cggc                                          24

<210> SEQ ID NO 194
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 194
gccgccggcc aaaggcacgg cggc                                          24

<210> SEQ ID NO 195
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 195
gccgccgaaa gcaaagccgg cggc                                          24

<210> SEQ ID NO 196
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 196
gccgccggca aagcaaacgg cggc                                          24

<210> SEQ ID NO 197
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 197
gccgccgaag caaagcacgg cggc                                          24

<210> SEQ ID NO 198
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 198
gccgccgagc aaagcaacgg cggc                                          24
```

<210> SEQ ID NO 199
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 199
gccgccagcc gaaacggcgg cggc                                              24

<210> SEQ ID NO 200
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 200
gccgccgccg aaacggcagg cggc                                              24

<210> SEQ ID NO 201
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 201
gccgccaaag ccaaaggcgg cggc                                              24

<210> SEQ ID NO 202
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 202
gccgccgcca aaggcaaagg cggc                                              24

<210> SEQ ID NO 203
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 203
gccgccaagc caaaggcagg cggc                                              24

<210> SEQ ID NO 204
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 204
gccgccagcc aaaggcaagg cggc                                              24

<210> SEQ ID NO 205
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 205
gccgccaaaa agcaaagcgg cggc                                      24

<210> SEQ ID NO 206
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 206
gccgccgcaa agcaaaaagg cggc                                      24

<210> SEQ ID NO 207
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 207
gccgccaaaa gcaaagcagg cggc                                      24

<210> SEQ ID NO 208
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 208
gccgccagca aagcaaaagg cggc                                      24

<210> SEQ ID NO 209
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 209
gccgccaaag caaagcaagg cggc                                      24

<210> SEQ ID NO 210
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 210
gccgccaagc aaagcaaagg cggc                                      24

<210> SEQ ID NO 211
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 211
gccgcagccg caaagcggcg cggc                                      24

<210> SEQ ID NO 212

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 212
gccgcgccgc aaagcggcag cggc                                              24

<210> SEQ ID NO 213
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 213
gccgcaaagc cgaaacggcg cggc                                              24

<210> SEQ ID NO 214
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 214
gccgcgccga aacggcaaag cggc                                              24

<210> SEQ ID NO 215
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 215
gccgcaagcc gaaacggcag cggc                                              24

<210> SEQ ID NO 216
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 216
gccgcagccg aaacggcaag cggc                                              24

<210> SEQ ID NO 217
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 217
gccgcaaaaa gccaaaggcg cggc                                              24

<210> SEQ ID NO 218
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 218
```

-continued gccgcgccaa aggcaaaaag cggc  24

<210> SEQ ID NO 219
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 219
gccgcaaaag ccaaaggcag cggc  24

<210> SEQ ID NO 220
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 220
gccgcagcca aaggcaaaag cggc  24

<210> SEQ ID NO 221
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 221
gccgcaaagc caaaggcaag cggc  24

<210> SEQ ID NO 222
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 222
gccgcaagcc aaaggcaaag cggc  24

<210> SEQ ID NO 223
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 223
gccgcaaaaa gcaaagcaag cggc  24

<210> SEQ ID NO 224
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 224
gccgcaagca aagcaaaaag cggc  24

<210> SEQ ID NO 225
<211> LENGTH: 24
<212> TYPE: DNA

```
<213> ORGANISM: Artificial Sequence
<220> FEATURE:
<223> OTHER INFORMATION: Synthetic oligonucleotide

<400> SEQUENCE: 225
gccgcaaaag caaagcaaag cggc                                              24

<210> SEQ ID NO 226
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 226
gccgcaaagc aaagcaaaag cggc                                              24

<210> SEQ ID NO 227
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 227
gccgcaagca gcaaagcgcg cggc                                              24

<210> SEQ ID NO 228
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 228
gccgcgcagc aaagcgcaag cggc                                              24

<210> SEQ ID NO 229
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 229
gccgcaagcg caaagcagcg cggc                                              24

<210> SEQ ID NO 230
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 230
gccgcgcgca aagcagcaag cggc                                              24

<210> SEQ ID NO 231
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 231
gccgcagcaa gcaaagcgcg cggc                                              24
```

<210> SEQ ID NO 232
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 232
gccgcgcaag caaagcgcag cggc                                          24

<210> SEQ ID NO 233
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 233
gccgcagcgc aaagcaagcg cggc                                          24

<210> SEQ ID NO 234
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 234
gccgcgcgca aagcaagcag cggc                                          24

<210> SEQ ID NO 235
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 235
gccgcagcag caaagcgcag cggc                                          24

<210> SEQ ID NO 236
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 236
gccgcagcgc aaagcagcag cggc                                          24

<210> SEQ ID NO 237
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 237
gccgcagcag caaagcagcg cggc                                          24

<210> SEQ ID NO 238
<211> LENGTH: 24
<212> TYPE: DNA
<213> ORGANISM: Artificial Sequence
<220> FEATURE:

<223> OTHER INFORMATION: Synthetic oligonucleotide

<400> SEQUENCE: 238
gccgcgcagc aaagcagcag cggc    24

<210> SEQ ID NO 239
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 239
gccgagccgc caaaggcggc cggc    24

<210> SEQ ID NO 240
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 240
gccggccgcc aaaggcggca cggc    24

<210> SEQ ID NO 241
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 241
gccgaaagcc gcaaagcggc cggc    24

<210> SEQ ID NO 242
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 242
gccggccgca aagcggcaaa cggc    24

<210> SEQ ID NO 243
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 243
gccgaagccg caaagcggca cggc    24

<210> SEQ ID NO 244
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 244
gccgagccgc aaagcggcaa cggc    24

```
<210> SEQ ID NO 245
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 245
gccgaaaaag ccgaaacggc cggc                                              24

<210> SEQ ID NO 246
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 246
gccggccgaa acggcaaaaa cggc                                              24

<210> SEQ ID NO 247
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 247
gccgaaaagc cgaaacggca cggc                                              24

<210> SEQ ID NO 248
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 248
gccgagccga aacggcaaaa cggc                                              24

<210> SEQ ID NO 249
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 249
gccgaaagcc gaaacggcaa cggc                                              24

<210> SEQ ID NO 250
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 250
gccgaagccg aaacggcaaa cggc                                              24

<210> SEQ ID NO 251
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 251
gccgaaaaag ccaaaggcaa cggc                                         24

<210> SEQ ID NO 252
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 252
gccgaagcca aaggcaaaaa cggc                                         24

<210> SEQ ID NO 253
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 253
gccgaaaagc caaggcaaa cggc                                          24

<210> SEQ ID NO 254
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 254
gccgaaagcc aaggcaaaa cggc                                          24

<210> SEQ ID NO 255
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 255
gccgaagcca gcaaagcggc cggc                                         24

<210> SEQ ID NO 256
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 256
gccggccagc aaagcggcaa cggc                                         24

<210> SEQ ID NO 257
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 257
gccgaagccg caaagcaggc cggc                                         24

<210> SEQ ID NO 258
<211> LENGTH: 24
```

<212> TYPE: DNA
<213> ORGANISM: Artificial Sequence
<220> FEATURE:
<223> OTHER INFORMATION: Synthetic oligonucleotide

<400> SEQUENCE: 258
gccggccgca aagcaggcaa cggc                                          24

<210> SEQ ID NO 259
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 259
gccgagccaa gcaaagcggc cggc                                          24

<210> SEQ ID NO 260
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 260
gccggccaag caaagcggca cggc                                          24

<210> SEQ ID NO 261
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 261
gccgagccgc aaagcaaggc cggc                                          24

<210> SEQ ID NO 262
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 262
gccggccgca aagcaaggca cggc                                          24

<210> SEQ ID NO 263
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 263
gccgagccag caaagcggca cggc                                          24

<210> SEQ ID NO 264
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 264
gccgagccgc aaagcaggca cggc                                            24

<210> SEQ ID NO 265
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 265
gccgagccag caaagcaggc cggc                                            24

<210> SEQ ID NO 266
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 266
gccggccagc aaagcaggca cggc                                            24

<210> SEQ ID NO 267
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 267
gccgaaaaag caaagcaaaa cggc                                            24

<210> SEQ ID NO 268
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 268
gccgaaaagc aaagcaaaaa cggc                                            24

<210> SEQ ID NO 269
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 269
gccgaagcag ccaaaggcgc cggc                                            24

<210> SEQ ID NO 270
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 270
gccggcagcc aaaggcgcaa cggc                                            24

<210> SEQ ID NO 271
<211> LENGTH: 24
<212> TYPE: DNA
<213> ORGANISM: Artificial Sequence

```
-continued

<220> FEATURE:
<223> OTHER INFORMATION: Synthetic oligonucleotide

<400> SEQUENCE: 271
gccgaagcgc caaaggcagc cggc                                              24

<210> SEQ ID NO 272
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 272
gccggcgcca aggcagcaa cggc                                               24

<210> SEQ ID NO 273
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 273
gccgagcaag ccaaaggcgc cggc                                              24

<210> SEQ ID NO 274
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 274
gccggcaagc caaaggcgca cggc                                              24

<210> SEQ ID NO 275
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 275
gccgagcgcc aaaggcaagc cggc                                              24

<210> SEQ ID NO 276
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 276
gccggcgcca aggcaagca cggc                                               24

<210> SEQ ID NO 277
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 277
gccgagcagc caaaggcgca cggc                                              24
```

<210> SEQ ID NO 278
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 278
gccgagcgcc aaaggcagca cggc                                          24

<210> SEQ ID NO 279
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 279
gccgagcagc caaaggcagc cggc                                          24

<210> SEQ ID NO 280
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 280
gccggcagcc aaaggcagca cggc                                          24

<210> SEQ ID NO 281
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 281
gccgaaaagc agcaaagcgc cggc                                          24

<210> SEQ ID NO 282
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 282
gccggcagca aagcgcaaaa cggc                                          24

<210> SEQ ID NO 283
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 283
gccgaaaagc gcaaagcagc cggc                                          24

<210> SEQ ID NO 284
<211> LENGTH: 24
<212> TYPE: DNA
<213> ORGANISM: Artificial Sequence
<220> FEATURE:
<223> OTHER INFORMATION: Synthetic oligonucleotide -continued

<400> SEQUENCE: 284
gccggcgcaa agcagcaaaa cggc                                           24

<210> SEQ ID NO 285
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 285
gccgagcaaa agcaaagcgc cggc                                           24

<210> SEQ ID NO 286
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 286
gccgagcgca aagcaaaagc cggc                                           24

<210> SEQ ID NO 287
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 287
gccggcaaaa gcaaagcgca cggc                                           24

<210> SEQ ID NO 288
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 288
gccggcgcaa agcaaaagca cggc                                           24

<210> SEQ ID NO 289
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 289
gccgaaagca agcaaagcgc cggc                                           24

<210> SEQ ID NO 290
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 290
gccggcaagc aaagcgcaaa cggc                                           24

<210> SEQ ID NO 291

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 291
gccgaaagcg caaagcaagc cggc                                          24

<210> SEQ ID NO 292
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 292
gccggcgcaa agcaagcaaa cggc                                          24

<210> SEQ ID NO 293
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 293
gccgaagcaa agcaaagcgc cggc                                          24

<210> SEQ ID NO 294
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 294
gccgaagcgc aaagcaaagc cggc                                          24

<210> SEQ ID NO 295
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 295
gccggcaaag caaagcgcaa cggc                                          24

<210> SEQ ID NO 296
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 296
gccggcgcaa agcaaagcaa cggc                                          24

<210> SEQ ID NO 297
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 297
```

```
gccgaaagca gcaaagcagc cggc                                              24
```

<210> SEQ ID NO 298
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 298

```
gccgaaagcg caaagcagca cggc                                              24
```

<210> SEQ ID NO 299
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 299

```
gccgaaagca gcaaagcgca cggc                                              24
```

<210> SEQ ID NO 300
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 300

```
gccggcagca aagcagcaaa cggc                                              24
```

<210> SEQ ID NO 301
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 301

```
gccgagcgca aagcagcaaa cggc                                              24
```

<210> SEQ ID NO 302
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 302

```
gccgagcagc aaagcgcaaa cggc                                              24
```

<210> SEQ ID NO 303
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 303

```
gccgagcaaa gcaaagcgca cggc                                              24
```

<210> SEQ ID NO 304
<211> LENGTH: 24
<212> TYPE: DNA

```
<213> ORGANISM: Artificial Sequence
<220> FEATURE:
<223> OTHER INFORMATION: Synthetic oligonucleotide

<400> SEQUENCE: 304
gccggcaaag caaagcagca cggc                                             24

<210> SEQ ID NO 305
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 305
gccgagcaaa gcaaagcagc cggc                                             24

<210> SEQ ID NO 306
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 306
gccgagcgca aagcaaagca cggc                                             24

<210> SEQ ID NO 307
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 307
gccgagcagc aaagcaaagc cggc                                             24

<210> SEQ ID NO 308
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 308
gccggcagca aagcaaagca cggc                                             24

<210> SEQ ID NO 309
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 309
gccgaagcag caaagcgcaa cggc                                             24

<210> SEQ ID NO 310
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 310
gccgaagcgc aaagcagcaa cggc                                             24
```

<210> SEQ ID NO 311
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 311
gccgagcaag caaagcaagc cggc                                              24

<210> SEQ ID NO 312
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 312
gccggcaagc aaagcaagca cggc                                              24

<210> SEQ ID NO 313
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 313
gccgaagcaa gcaaagcgca cggc                                              24

<210> SEQ ID NO 314
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 314
gccgaagcgc aaagcaagca cggc                                              24

<210> SEQ ID NO 315
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 315
gccgaagcaa gcaaagcagc cggc                                              24

<210> SEQ ID NO 316
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 316
gccggcaagc aaagcagcaa cggc                                              24

<210> SEQ ID NO 317
<211> LENGTH: 24
<212> TYPE: DNA
<213> ORGANISM: Artificial Sequence
<220> FEATURE:

<223> OTHER INFORMATION: Synthetic oligonucleotide

<400> SEQUENCE: 317
gccgagcaag caaagcgcaa cggc                                          24

<210> SEQ ID NO 318
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 318
gccgagcgca aagcaagcaa cggc                                          24

<210> SEQ ID NO 319
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 319
gccgaagcag caaagcaagc cggc                                          24

<210> SEQ ID NO 320
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 320
gccggcagca aagcaagcaa cggc                                          24

<210> SEQ ID NO 321
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 321
gccgaagcag caaagcagca cggc                                          24

<210> SEQ ID NO 322
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 322
gccgagcagc aaagcagcaa cggc                                          24

<210> SEQ ID NO 323
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 323
gccgagcaag caaagcagca cggc                                          24

```
<210> SEQ ID NO 324
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 324
gccgagcagc aaagcaagca cggc                                              24

<210> SEQ ID NO 325
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 325
gccgccgccg                                                              10

<210> SEQ ID NO 326
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 326
aaaaaaaaaa aaaaa                                                        15
```

SELECTION OF APTAMERS BASED ON GEOMETRY

CROSS REFERENCE TO RELATED APPLICATIONS

This application claims the benefit of U.S. Application No. 60/870,493, filed Dec. 18, 2006, the entirety of which is incorporated by reference herein.

BACKGROUND OF THE INVENTION

Various scientific and patent publications are referred to herein. Each is incorporated by reference in its entirety.

Aptamers are molecules that assume an appropriate shape "to fit" another molecule as in a lock and key mechanism. Aptamers can be used as diagnostic tools and/or therapeutics. They were first described in connection with a selection process called SELEX in 1990 by Tuerk and Gold (1). SELEX and its derivatives are based on starting with a large pool of molecules and enriching the pool through a series of iterations until the best binders are discovered. While this process has aided in the discovery of a number of high affinity binders, it is also cumbersome from the need to perform successive rounds of selection and amplification, ending with sequencing and testing of the sequenced aptamers (2). It is further complicated in that aptamers discovered through SELEX may not possess the desired attributes. For example, in the recent description of Cooperative Probe Assays and Tentacle Probes, low affinity binders may be preferable over high affinity binders in order to achieve greater specificity (3). Also the aptamers may need to be in a form such that they can undergo conformational changes producing an increase in signal. Thus there is a need for aptamer selection methods which are faster and easier than conventional SELEX and that allow selection of aptamers based on other properties than high affinity.

Aptamer selection on a chip has been suggested (4). This approach has particular appeal due to the fact that a library of aptamers can be screened for selection and counterselection in a matter of hours, yielding not only information about which sequences function as aptamers, but also information on affinities and/or thermodynamic properties. Unfortunately, chip screening is limited due to library size. Until now, incomplete screenings have been performed requiring multiple steps (5) or using aptamers that are unusually small (hexamers) (4). It is conceivable that mathematical models could screen the library if appropriate algorithms were available, reducing the library to a size that could be placed on a chip. But to date, no algorithms exist that can sufficiently enrich the pool. And given that a 100 mer aptamer contains over 1e60 possible structures and even a library of 20mers contains over 1e12 possibilities, present day computers could not perform all of the computations even if such an algorithm were to exist. The present invention has significant utility for chip based aptamer selection and enables the use of an enriched pool of nucleic acid sequences to define protein binding using both monovalent and multivalent constructs.

SUMMARY OF THE INVENTION

The present invention relates, in part, to the selection of aptamers based on geometries to bypass SELEX.

One aspect of the present invention provides for an algorithm for constructing a library of all possible aptamer geometries. Applications of the algorithm include, but are not limited to, design of tentacle probes, cooperative probe assays, drug constructs, cell targeting constructs, and synthetic antibodies.

Another aspect of the present invention pertains to use of statistical data on current aptamers to further enrich the geometries to those which are most likely to bind.

In certain embodiments, the present invention provides a process of geometric selection of aptamers on a chip. The process includes the steps of choosing an objective parameter for aptamer design, such as specificity, affinity, kinetics, inhibition, among others. In one aspect, an ideal size or range of sizes for a given aptamer is chosen. In another aspect, a pool is created based on desirable geometries. In some embodiments the desired geometries are all possible geometries, but in others a smaller subset of geometries may be used. In yet another aspect, the number of possible sequences possessing those geometries is reduced by further algorithims, such as GC content in stem and/or loop. In still another aspect, all or a part of the library is placed upon a chip with each sequence at a discrete location. In some embodiments, specific and nonspecific analyte are passed over the chip. In some embodiments, fluorescence is used to determine binding and binding characteristics.

In certain embodiments, the aptamers described are composed of nucleic acids and/or nucleic acid analogues such as PNA's and LNA's.

In further embodiments, the use of chip based selection can be applied to pairs or greater numbers of aptamers, where geometrically selected aptamers are placed in close proximity to each other either through attachment to a substrate or via linker. This provision allows screening for desirable aptamer qualities from cooperative or destructive interactions from pairs of aptamers.

The present invention further relates to a kit for aptamer selection to a target analyte in a sample. The kit comprises one or more geometrically selected aptamers in the present invention. The kit can also comprise instructions on their use. When used in chip based selection, the kit may also contain a chip and reagents.

Other aspects of the present invention are described throughout the specification.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF THE INVENTION

Figure 1:
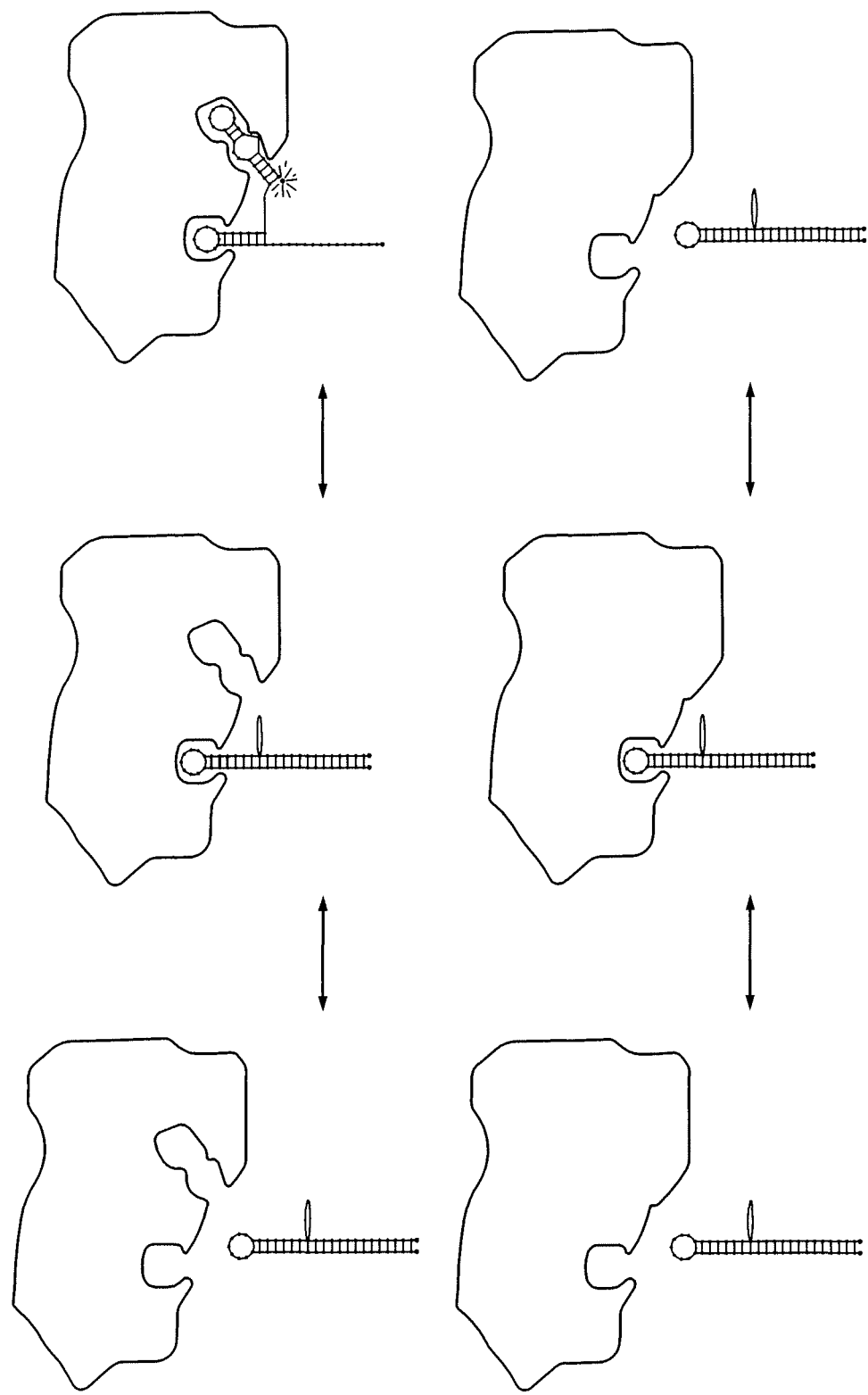
FIG. 1 depicts a probe that utilizes two relatively short or low affinity aptamers in order to achieve the desired specificity, where binding only occurs to a wild type analyte, and where the exemplary probe allows for changes in conformation in order to produce a change in fluorescent signal resulting in detection.
Figure 2:
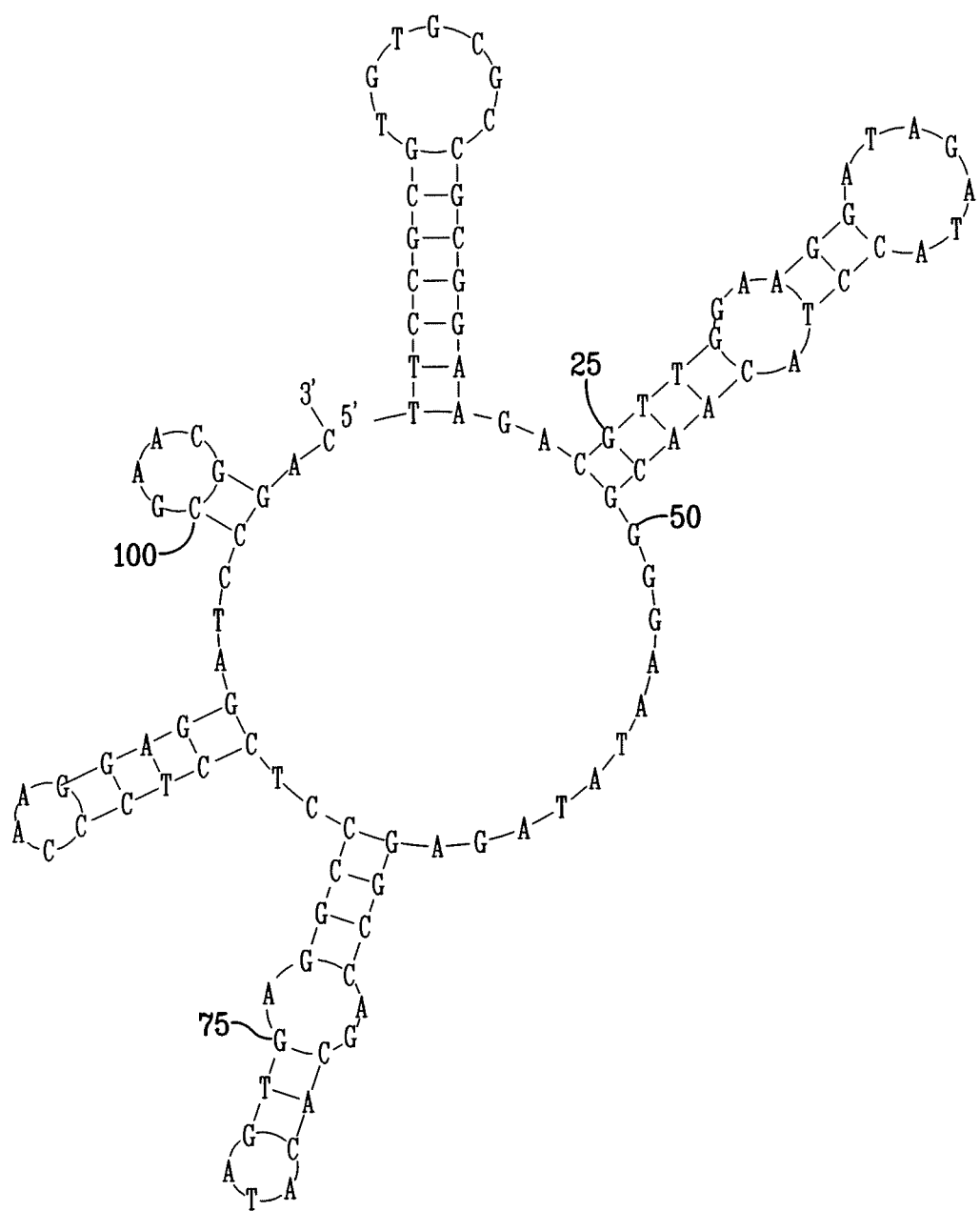
FIG. 2 depicts a dopamine aptamer, additionally depicting a series of short aptamers linked together cooperatively via single stranded DNA, and where the stem content may be described as primarily GC content forming the most stable conformation of the given aptamer geometries.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

As used in this disclosure, the singular forms "a", "an", and "the" may refer to plural articles unless specifically stated otherwise. Thus, for example, references to a method of manufacturing, derivatizing, or treating "an analyte" may include a mixture of one or more analytes. Furthermore, the use of grammatical equivalents such as "nucleic acids", "polynucleotides", or "oligonucleotides" are not meant to imply differences among these terms unless specifically indicated.

To facilitate understanding of the invention set forth in the disclosure that follows, a number of terms are defined below.
Terms The term "aptamer" refers to a molecule or series of molecules which assumes a shape that contributes toward binding of a target molecule or organism.

The term "complementary strand" refers to a strand composed of opposite molecules in a pair as compared with the first strand. The pair will exhibit affinity for each other such as in electrostatic, hydrophobic, hydrophilic, magnetic or hydrogen bonding interactions. A common example of complementarity is in nucleic acid base pairing.

The term "cooperativity" refers to the use of two or more aptamers in a set, where a binding event to one aptamer results in the presentation of bound analyte at an enhanced local concentration to a second aptamer, resulting in increases in kinetics, affinity, sensitivity and/or specificity of the reaction over what the second aptamer or set of aptamers would experience in a noncooperative setting such as in free solution. Cooperativity can refer to enhanced characteristics contributing to the binding of an analyte or the inhibition of binding of an analyte. A cooperative aptamer is one that has two or more aptamers in close proximity that act cooperatively.

The term "geometric enrichment" refers to the preselection of aptamers based on unique geometries. For a 20mer aptamer this corresponds to approximately 325 unique geometries in contrast with more than 1e12 randomers used in SELEX. Geometric enrichment may refer to selection or consideration of all possible geometries or only a fraction of those geometries.

The term "characteristic" refers to length, mass, volume, composition, geometry, or shape. As an example, a characteristic of an aptamer is the aptamer's length.

The terms "insertion" and "deletion" refer to extra or missing molecules in a complementary strand respectively.

The term "label" refers to any atom or molecule that can be attached to a molecule for detection.

The term "ligand" refers to any binder whether biological or non-biological of a target entity.

The term "loop" refers to a single stranded segment of aptamer that is created by the aptamer folding back on itself.

The term "microarray" refers to two or more unique aptamers or combinations of aptamers in a single screening in which target binding to one aptamer or combination of aptamers is distinguishable from binding to the others.

The term "mismatch" in aptamer folding refers to a molecule in a complementary strand which does not allow for binding of the molecule opposite of it. In an aptamer-target complex, a mismatch indicates a variant target other than the wild type.

The terms "peptide", "polypeptide", "oligopeptide", or "protein" refers to two or more covalently linked, naturally occurring or synthetically manufactured amino acids. There is no intended distinction between the length of a "peptide", "polypeptide", "oligopeptide", or "protein".

The term "peptide nucleic acid" or "PNA" refers to an analogue of DNA that has a backbone that comprises amino acids or derivatives or analogues thereof, rather than the sugar-phosphate backbone of nucleic acids (DNA and RNA). PNA mimics the behavior of a natural nucleic acid and binds complementary nucleic acid strands.

The term "pocket" refers to a single stranded segment of the aptamer that is created by mismatches, insertions or deletions in the complementary strand of the aptamer.

The terms "polynucleotide", "oligonucleotide" or "nucleic acid" refer to polydeoxyribonucleotides (DNA), polyribonucleotides (RNA), analogs and derivatives thereof. There is no intended distinction between the length of a "polynucleotide", "oligonucleotide" or "nucleic acid".

A "small organic molecule" is a carbon-containing molecule which is typically less than about 2000 daltons. More typically, the small organic molecule is a carbon-containing molecule of less than about 1000 daltons. The small organic molecule may or may not be a biomolecule with known biological activity.

The term "stem" refers to a region of the aptamer which is folded on itself due to interactions between complementary strands.

The term "substrate" refers to a medium relatively large to the aptamer and can include the surface of a solid support, a nanotube, a cell, or a microorganism such as a bacterium, virus, or phage. Suitable solid supports include, but are not limited to cyclo olefin polymers and copolymers, acrylamide, cellulose, nitrocellulose, glass, polystyrene, polyethylene vinyl acetate, polypropylene, polymethacrylate, polyethylene, polysilicates, polyethylene oxide, polycarbonates, teflon, fluorocarbons, nylon, silicon rubber, collagen, polyanhydrides, polyglycolic acid, polylactic acid, polyorthoesters, polypropylfumarate, glycosaminoglycans, and polyamino acids. A solid support or matrix can be in one of the many useful forms including thin films or membranes, plates such as various formats of microtiter plates, beads such as magnetic beads or latex beads, bottles, dishes, fibers, woven fibers, shaped polymers, particles, microarrays, microfluidic channels, microchips, microparticles such as microspheres, and nanoparticles. Methods of attaching the capture and detection and capture probes to a surface are known in the art and include, without limitation, direct adhesion to the surface such as plastic, use of a capture agent, chemical coupling, and via a binding pair such as biotin-avidin. The detection and capture probes can independently have a tether to facilitate the attachments to the surface signals.

The term "target" has reference to the molecule, compound or organism an aptamer is designed to bind. Appropriate targets include both biological and non-biological entities. Suitable biological targets include, but are not limited to, proteins, peptides, nucleic acid sequences, peptide nucleic acids, antibodies, antigens, receptors, molecules, biological cells, microorganisms, cellular organelles, cell membrane fragments, bacteriophage, bacteriophage fragments, whole viruses, viral fragments, and small molecules such as lipids, carbohydrates, amino acids, drug substances, and molecules for biological screening and testing. A target can also refer to a complex of two or more molecules, for example, a ribosome with both RNA and protein elements or an enzyme with substrate attached.

The term "tentacle probe" refers to a type of cooperative probe having a detection probe and a capture probe wherein the detection probe can change conformation and the change in conformation generates a change in detectable signal. In general, upon binding to a target analyte, the interactions between the detection probe and the target analyte shifts the equilibrium predominantly towards to an open conformation.

The term "variant" or "mutant" analyte refers to an analyte that is different than its wildtype counterpart.

The term "wildtype" as used herein refers to the typical form of an organism, strain, gene, or characteristic as it occurs in nature, as distinguished from mutant forms that can result from selective breeding In a first aspect, the present invention discloses methods for selecting one or more aptamers by geometric enrichment, comprising consideration of one or more characteristics of the one or more aptamers to so as to formulate one or more possible geometries of the one or more aptamers. Additional detail regarding such methods is set forth in additional detail elsewhere herein. In some embodiments, the methods include consideration of more than 1% of all possible geometries for a given aptamer length. In other embodiments, the methods may include more than 10% of all possible geometries for a given aptamer length. In any of these embodiments, the GC content of a stem may be greater, on average, than 50%.

The claimed methods also include performing additional geometric enrichment on a substrate. Suitable substrates include glass, polymers, and the like; substrates suitable for forming microarrays are considered especially suitable. In some embodiments, attachment of one or more aptamers—preferably chosen or identified by geometric enrichment—are used to form a microarray.

Geometric enrichment may include monitoring binding to the microarray via fluorescence. Techniques for such monitoring are known to those having ordinary skill in the art. In some configurations, the contrast between wild type and variant binding is used to select aptamers.

Binding over time of aptamers may also be used to determine the kinetics of individual aptamers. In some embodiments, binding over multiple concentrations of one or more aptamers is used to determine aptamer affinities.

Further, binding may also be used to determine inhibition of a process, which processes may be enzymatic in nature. Binding may also be used to determine the acceleration of a process, including enzymatic processes.

Geometric enrichment may suitably be performed on a substrate, as described elsewhere herein. Such substrates may comprise microarrays. Enrichment may be performed by monitoring binding to the microarray via fluorescence, which may include using the contrast between wild type and variant binding is used to select aptamers. Binding over time may also be used to observe kinetics of individual aptamers and, in some cases, to determine aptamer affinities, and or the inhibition or acceleration of processes, including enzymatic processes.

Two or more geometric enrichment-selected aptamers are linked directly or indirectly for further enrichment. One or more of such aptamers may be linked to a substrate so as to form a microarray, which microarray may be used to support enrichment, as described elsewhere herein.

Aptamers—including aptamers selected by geometric enrichment—may also be linked to one or more ligands. Such ligands may be identified or isolated by a variety of methods known to those having ordinary skill in the art. Aptamer-ligand combinations may be linked to a substrate to form a microarray, having application as described elsewhere herein.

The claimed invention also provides kits, which kits include one or more geometrically enriched aptamers according to the claimed methods. Such kits may be used to the method of claim 1 and instructions for using them to select the appropriate aptamer. Kits suitably include instructions to enable to user to utilize the kits, although proper use of the kits will be apparent to those of ordinary skill in the art. Kits may include one or more geometrically enrichment selected aptamers—which may also include ligands.

Additional discussion of the claimed invention follows.

Geometric Enrichment

As discussed, the claimed invention includes a method for selecting aptamers using geometric enrichment.

In geometric enrichment, all the possible geometries are formulated for a given aptamer length or for a range of aptamer lengths. There are a number of methods in which this range of geometries can be produced.

One example of a method to produce the available geometries involves making note of minimum requirements for aptamer geometry formation. For example, a stem cannot form without at least one base pair forming; a pocket cannot exist without at least one base failing to base pair; the loop on the end of an aptamer cannot be shorter than three base pairs and still fold on itself.

In other embodiments, the geometries can be further refined by examining statistical trends among existing aptamers. For example, in a survey of 32 different aptamers with affinities toward 21 different targets, the following statistics were observed (6-26):

|  | Bases in folded region | Number of loops in folded region | Loop Size | Number of pockets | Pocket Size | Number of Stems | Stem Size |
| --- | --- | --- | --- | --- | --- | --- | --- |
| Average | 24.26875 | 1 | 6.385938 | 0.870313 | 3.247378 | 1.870313 | 4.311406 |
| St Dev | 15.01247 | 0 | 5.209014 | 1.192218 | 1.874825 | 1.192218 | 1.191662 |
| Minimum | 9 | 1 | 3 | 0 | 1 | 1 | 2 |
| Maximum | 70 | 1 | 21 | 5 | 8 | 6 | 7.3 |

By using the number of bases in each folded region (aptamer) one can ascertain the average number of loops, pockets and stems per base in the aptamer. One can also determine the standard deviations of these occurrences. Accordingly, in some embodiments, these aptamer statistics can be used to further reduce the number of possible geometries. For example, it can be observed that there were no stem sizes below 2 bases in length. Using this statistic, and the statistic on minimum loop size, it can be deduced that there can be no more than three pockets and one loop in a 20mer aptamer.

Figure 3:
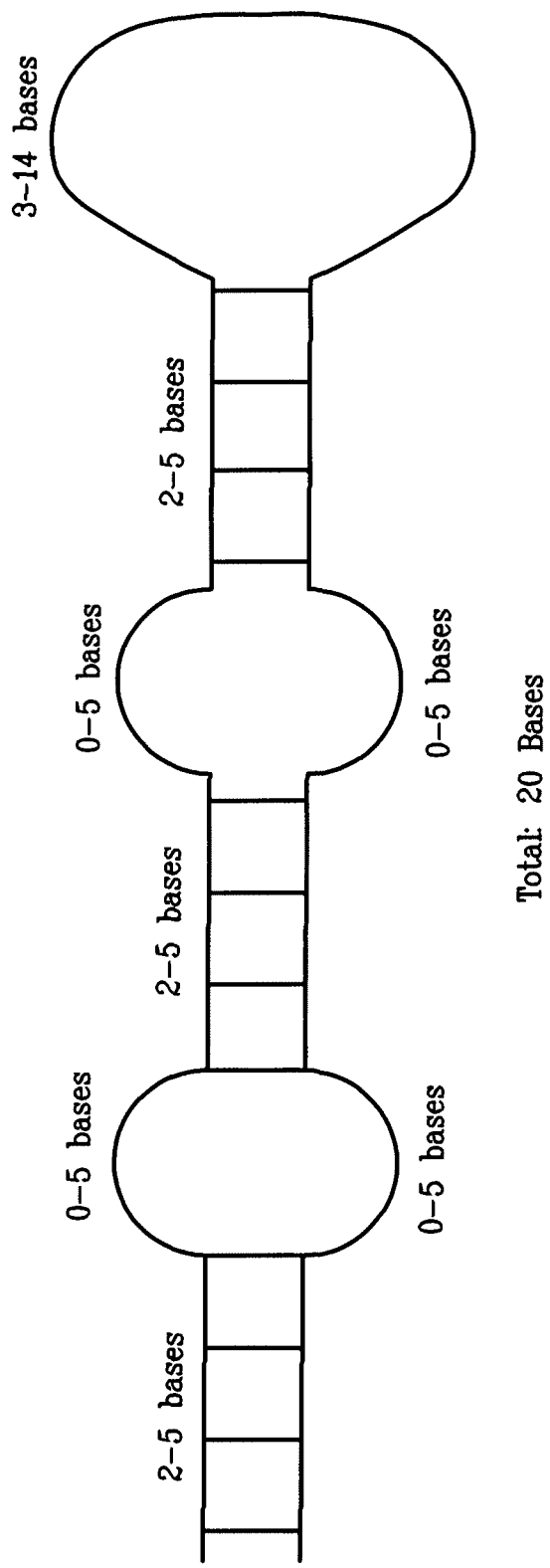
FIG. 3 depicts a design algorithm for a 20-mer aptamer, in which the minimum stem size is 2 bases as necessary to stabilize geometry, in which pocket sizes vary between 0 and 5 bases and are not necessarily symmetrical, in which the minimum loop size that will still allow for folding is 3 bases.

One method of creating the list of all possible geometries is to use these rules to create a figure for a given aptamer size as shown in FIG. 3. A table is made as set forth in Example I, in which all the possible combinations defined in the figure are mapped out.

It should be noted that in some embodiments it is not necessary to use all the available geometries. In some embodiments, suspected geometries targeting a given epitope can be the focus of selection.

Suitable aptamer sizes for geometric enrichment are typically between 5 and 1000 bases, between 10 and 200 bases, between 10 and 100 bases.

Further Enrichment

Similar to geometric enrichment, in some embodiments statistical data can be used to further enrich the possible aptamer pool. For example, in a survey of 32 different aptamers with affinities toward 21 different targets, the following statistics were observed (6-26):

|  | Loop GC content | Pocket GC content | Stem GC content |
| --- | --- | --- | --- |
| Average | 0.387059 | 0.500207 | 0.689641 |
| St Dev | 0.1804 | 0.234697 | 0.17954 |
| Minimum | 0 | 0 | 0.25 |
| Maximum | 0.89 | 1 | 1 |

By using this data, it is seen that stem GC content may be comparatively high. In fact, in some embodiments, it is preferred to use a GC rich stem greater than 50%, greater than 60%, greater than 75% or even 100% GC rich. Such a stem stabilizes the aptamer geometry more than any other shape. By selecting stem with high GC content, the number of possible sequences conforming to a given geometry is greatly reduced, easily allowing chip selection of aptamers.

This same methodology can be applied to loop content as well. In some embodiments, loop content may have less than 50% GC content, less than 40% GC content, less than 30% GC content.

Microarray Based Selection

In some embodiments, aptamer selection through geometric enrichment is greatly simplified by using an aptamer microarray. In some embodiments a library of similar geometries with identical or varying base content is placed on the microarray. In other embodiments, many different geometries with identical or varying base content are placed on the microarray. In some embodiments, the number of geometries represented on the microarray is greater than 1%, greater than 10%, or even greater than 50% of the possible geometries.

In some embodiments, target is allowed to hybridize with the aptamers on the microarray. In embodiments where target is labeled with a fluorescent substance, the excess target is washed away following hybridization. Those geometries which exhibit the greatest fluorescence above background are chosen as candidate aptamers.

In other embodiments, variant is allowed to hybridize with the aptamers on the microarray. In embodiments where variant is labeled with a fluorescent substance, the excess variant is washed away following hybridization. Those geometries which exhibit fluorescence above background are eliminated as possible aptamers.

In other embodiments it may be desirable to have aptamers that bind to both the wild type and variant. In this case, those geometries that exhibit binding to both the wild type and variant in microarray analysis are chosen as candidate aptamers.

In still other embodiments, the microarray format is used to measure kinetic parameters of the aptamers before selection. In some embodiments, the microarray is monitored through label free detection means such as fluorescent polarization or Surface Plasmon Resonance. Binding over time is monitored to determine kinetic rates. Those aptamers exhibiting the desired degree of binding and at the desired rate are selected as candidate aptamers.

In yet other embodiments, thermodynamic parameters such as the affinity of binding are gleaned from the microarray. In some embodiments, the forward and reverse rate constants are determined as previously mentioned. The ratio of the forward to the reverse rate constant is used to find the affinity. In other embodiments, titrations of wild type target can be used to measure the fluorescence as a function of concentration. For an excess of target, the concentration at which binding is half maximal is equivalent to the dissociation constant.

Microarray Based Selection of Multivalent Aptamers

In some embodiments, it may be desirable to enhance the performance of individual aptamers by combining them with other aptamers. In some embodiments, geometrically enriched aptamers are placed in groups of two or more prior to selection. Methods of placement together include but are not limited to indirect linkage to a substrate or direct linkage via polyethylene glycol, carbon chains, natural or modified nucleic acids, amino acids, or other linkers known to those skilled in the art.

In some embodiments, the aptamers selected from an initial round of geometric enrichment may be placed together in a microarray. In some embodiments, geometrically enriched and selected aptamers are placed in groups of two or more prior to selection. Methods of placement together include but are not limited to indirect linkage to a substrate or direct linkage via polyethylene glycol, carbon chains, natural or modified nucleic acids, amino acids, or other linkers known to those skilled in the art.

In some embodiments, target is allowed to hybridize with the aptamers on the microarray. In embodiments where target is labeled with a fluorescent substance, the excess target is washed away following hybridization. Those geometries which exhibit the greatest fluorescence above background are chosen as candidate aptamers.

In other embodiments, variant is allowed to hybridize with the aptamers on the microarray. In embodiments where variant is labeled with a fluorescent substance, the excess variant is washed away following hybridization. Those geometries which exhibit fluorescence above background are eliminated as possible aptamers.

In other embodiments it may be desirable to have aptamers that bind to both the wild type and variant. In this case, those geometries that exhibit binding to both the wild type and variant in microarray analysis are chosen as candidate aptamers.

In still other embodiments, the microarray format can be used to measure kinetic parameters of the aptamers before selection. In some embodiments, the microarray is monitored through label free detection means such as fluorescent polarization or Surface Plasmon Resonance. Binding over time is monitored to determine kinetic rates. Those aptamers exhibiting the desired degree of binding and at the desired rate are selected as candidate aptamers.

In yet other embodiments, thermodynamic parameters such as the affinity of binding are gleaned from the microarray. In some embodiments, the forward and reverse rate constants are determined as previously mentioned. The ratio of the forward to the reverse rate constant is used to find the affinity. In other embodiments, titrations of wild type target can be used to measure the fluorescence as a function of concentration. For an excess of target, the concentration at which binding is half maximal is equivalent to the dissociation constant.

EXAMPLES AND ILLUSTRATIVE EMBODIMENTS

Example I

Example of Creating all Possible Geometries for an Aptamer

In an exemplary embodiment of creating all possible geometries, the format shown in FIG. 3 was used to create all possible geometries for a 20mer. In the table below, Seq #, L, S1, S2, S3, P1, P2, P3, P4 stand for sequence number, loop, stem 1, stem 2, stem 3, pocket 1, pocket 2, pocket 3, pocket 4 respectively. The numbers beside each sequence number represent the number of bases comprising each feature. Each row adds up to a total of 20 bases in the aptamer. The location of each feature in the exemplary geometric aptamer is as shown in FIG. 3.

| Seq # | L | S1 | S2 | S3 | P1 | P2 | P3 | P4 |
|---|---|---|---|---|---|---|---|---|
| 1 | 10 | 10 | 0 | 0 | 0 | 0 | 0 | 0 |
| 2 | 9 | 6 | 4 | 0 | 1 | 0 | 0 | 0 |
| 3 | 9 | 6 | 4 | 0 | 0 | 1 | 0 | 0 |
| 4 | 9 | 4 | 6 | 0 | 1 | 0 | 0 | 0 |
| 5 | 9 | 4 | 6 | 0 | 0 | 1 | 0 | 0 |
| 6 | 9 | 4 | 4 | 0 | 3 | 0 | 0 | 0 |
| 7 | 9 | 4 | 4 | 0 | 0 | 3 | 0 | 0 |
| 8 | 9 | 4 | 4 | 0 | 2 | 1 | 0 | 0 |
| 9 | 9 | 4 | 4 | 0 | 1 | 2 | 0 | 0 |
| 10 | 8 | 12 | 0 | 0 | 0 | 0 | 0 | 0 |
| 11 | 8 | 6 | 4 | 0 | 2 | 0 | 0 | 0 |
| 12 | 8 | 6 | 4 | 0 | 0 | 2 | 0 | 0 |
| 13 | 8 | 6 | 4 | 0 | 1 | 1 | 0 | 0 |
| 14 | 8 | 4 | 6 | 0 | 2 | 0 | 0 | 0 |
| 15 | 8 | 4 | 6 | 0 | 0 | 2 | 0 | 0 |
| 16 | 8 | 4 | 6 | 0 | 1 | 1 | 0 | 0 |
| 17 | 8 | 4 | 4 | 0 | 4 | 0 | 0 | 0 |
| 18 | 8 | 4 | 4 | 0 | 0 | 4 | 0 | 0 |
| 19 | 8 | 4 | 4 | 0 | 3 | 1 | 0 | 0 |
| 20 | 8 | 4 | 4 | 0 | 1 | 3 | 0 | 0 |
| 21 | 8 | 4 | 4 | 0 | 2 | 2 | 0 | 0 |
| 22 | 7 | 8 | 4 | 0 | 1 | 0 | 0 | 0 |
| 23 | 7 | 8 | 4 | 0 | 0 | 1 | 0 | 0 |
| 24 | 7 | 6 | 6 | 0 | 1 | 0 | 0 | 0 |
| 25 | 7 | 6 | 6 | 0 | 0 | 1 | 0 | 0 |
| 26 | 7 | 6 | 4 | 0 | 3 | 0 | 0 | 0 |
| 27 | 7 | 6 | 4 | 0 | 0 | 3 | 0 | 0 |
| 28 | 7 | 6 | 4 | 0 | 2 | 1 | 0 | 0 |
| 29 | 7 | 6 | 4 | 0 | 1 | 2 | 0 | 0 |
| 30 | 7 | 4 | 8 | 0 | 1 | 0 | 0 | 0 |
| 31 | 7 | 4 | 8 | 0 | 0 | 1 | 0 | 0 |
| 32 | 7 | 4 | 6 | 0 | 3 | 0 | 0 | 0 |
| 33 | 7 | 4 | 6 | 0 | 0 | 3 | 0 | 0 |
| 34 | 7 | 4 | 6 | 0 | 2 | 1 | 0 | 0 |
| 35 | 7 | 4 | 6 | 0 | 1 | 2 | 0 | 0 |
| 36 | 7 | 4 | 4 | 0 | 5 | 0 | 0 | 0 |
| 37 | 7 | 4 | 4 | 0 | 0 | 5 | 0 | 0 |
| 38 | 7 | 4 | 4 | 0 | 4 | 1 | 0 | 0 |
| 39 | 7 | 4 | 4 | 0 | 1 | 4 | 0 | 0 |
| 40 | 7 | 4 | 4 | 0 | 3 | 2 | 0 | 0 |
| 41 | 7 | 4 | 4 | 0 | 2 | 3 | 0 | 0 |
| 42 | 6 | 14 | 0 | 0 | 0 | 0 | 0 | 0 |
| 43 | 6 | 8 | 4 | 0 | 2 | 0 | 0 | 0 |
| 44 | 6 | 8 | 4 | 0 | 0 | 2 | 0 | 0 |
| 45 | 6 | 8 | 4 | 0 | 1 | 1 | 0 | 0 |
| 46 | 6 | 6 | 6 | 0 | 2 | 0 | 0 | 0 |
| 47 | 6 | 6 | 6 | 0 | 0 | 2 | 0 | 0 |
| 48 | 6 | 6 | 6 | 0 | 1 | 1 | 0 | 0 |
| 49 | 6 | 6 | 4 | 0 | 4 | 0 | 0 | 0 |
| 50 | 6 | 6 | 4 | 0 | 0 | 4 | 0 | 0 |
| 51 | 6 | 6 | 4 | 0 | 3 | 1 | 0 | 0 |
| 52 | 6 | 6 | 4 | 0 | 1 | 3 | 0 | 0 |
| 53 | 6 | 6 | 4 | 0 | 2 | 2 | 0 | 0 |
| 54 | 6 | 4 | 8 | 0 | 2 | 0 | 0 | 0 |
| 55 | 6 | 4 | 8 | 0 | 0 | 2 | 0 | 0 |
| 56 | 6 | 4 | 8 | 0 | 1 | 1 | 0 | 0 |
| 57 | 6 | 4 | 6 | 0 | 4 | 0 | 0 | 0 |
| 58 | 6 | 4 | 6 | 0 | 0 | 4 | 0 | 0 |
| 59 | 6 | 4 | 6 | 0 | 3 | 1 | 0 | 0 |
| 60 | 6 | 4 | 6 | 0 | 1 | 3 | 0 | 0 |
| 61 | 6 | 4 | 6 | 0 | 2 | 2 | 0 | 0 |
| 62 | 6 | 4 | 4 | 0 | 5 | 1 | 0 | 0 |
| 63 | 6 | 4 | 4 | 0 | 1 | 5 | 0 | 0 |
| 64 | 6 | 4 | 4 | 0 | 4 | 2 | 0 | 0 |
| 65 | 6 | 4 | 4 | 0 | 2 | 4 | 0 | 0 |
| 66 | 6 | 4 | 4 | 0 | 3 | 3 | 0 | 0 |
| 67 | 6 | 4 | 4 | 4 | 1 | 0 | 1 | 0 |
| 68 | 6 | 4 | 4 | 4 | 0 | 1 | 1 | 0 |
| 69 | 6 | 4 | 4 | 4 | 1 | 0 | 0 | 1 |
| 70 | 6 | 4 | 4 | 4 | 0 | 1 | 0 | 1 |
| 71 | 5 | 8 | 6 | 0 | 1 | 0 | 0 | 0 |
| 72 | 5 | 8 | 6 | 0 | 0 | 1 | 0 | 0 |
| 73 | 5 | 8 | 4 | 0 | 3 | 0 | 0 | 0 |
| 74 | 5 | 8 | 4 | 0 | 0 | 3 | 0 | 0 |
| 75 | 5 | 8 | 4 | 0 | 2 | 1 | 0 | 0 |

-continued

| Seq # | L | S1 | S2 | S3 | P1 | P2 | P3 | P4 |
|---|---|---|---|---|---|---|---|---|
| 76 | 5 | 8 | 4 | 0 | 1 | 2 | 0 | 0 |
| 77 | 5 | 6 | 8 | 0 | 1 | 0 | 0 | 0 |
| 78 | 5 | 6 | 8 | 0 | 0 | 1 | 0 | 0 |
| 79 | 5 | 6 | 6 | 0 | 3 | 0 | 0 | 0 |
| 80 | 5 | 6 | 6 | 0 | 0 | 3 | 0 | 0 |
| 81 | 5 | 6 | 6 | 0 | 2 | 1 | 0 | 0 |
| 82 | 5 | 6 | 6 | 0 | 1 | 2 | 0 | 0 |
| 83 | 5 | 6 | 4 | 0 | 5 | 0 | 0 | 0 |
| 84 | 5 | 6 | 4 | 0 | 0 | 5 | 0 | 0 |
| 85 | 5 | 6 | 4 | 0 | 4 | 1 | 0 | 0 |
| 86 | 5 | 6 | 4 | 0 | 1 | 4 | 0 | 0 |
| 87 | 5 | 6 | 4 | 0 | 3 | 2 | 0 | 0 |
| 88 | 5 | 6 | 4 | 0 | 2 | 3 | 0 | 0 |
| 89 | 5 | 4 | 10 | 0 | 1 | 0 | 0 | 0 |
| 90 | 5 | 4 | 10 | 0 | 0 | 1 | 0 | 0 |
| 91 | 5 | 4 | 8 | 0 | 3 | 0 | 0 | 0 |
| 92 | 5 | 4 | 8 | 0 | 0 | 3 | 0 | 0 |
| 93 | 5 | 4 | 8 | 0 | 2 | 1 | 0 | 0 |
| 94 | 5 | 4 | 8 | 0 | 1 | 2 | 0 | 0 |
| 95 | 5 | 4 | 6 | 0 | 5 | 0 | 0 | 0 |
| 96 | 5 | 4 | 6 | 0 | 0 | 5 | 0 | 0 |
| 97 | 5 | 4 | 6 | 0 | 4 | 1 | 0 | 0 |
| 98 | 5 | 4 | 6 | 0 | 1 | 4 | 0 | 0 |
| 99 | 5 | 4 | 6 | 0 | 3 | 2 | 0 | 0 |
| 100 | 5 | 4 | 6 | 0 | 2 | 3 | 0 | 0 |
| 101 | 5 | 4 | 4 | 4 | 2 | 0 | 1 | 0 |
| 102 | 5 | 4 | 4 | 4 | 0 | 2 | 1 | 0 |
| 103 | 5 | 4 | 4 | 4 | 2 | 0 | 0 | 1 |
| 104 | 5 | 4 | 4 | 4 | 0 | 2 | 0 | 1 |
| 105 | 5 | 4 | 4 | 4 | 1 | 0 | 2 | 0 |
| 106 | 5 | 4 | 4 | 4 | 0 | 1 | 2 | 0 |
| 107 | 5 | 4 | 4 | 4 | 1 | 0 | 0 | 2 |
| 108 | 5 | 4 | 4 | 4 | 0 | 1 | 0 | 2 |
| 109 | 5 | 4 | 4 | 4 | 1 | 1 | 1 | 0 |
| 110 | 5 | 4 | 4 | 4 | 1 | 1 | 0 | 1 |
| 111 | 5 | 4 | 4 | 4 | 1 | 0 | 1 | 1 |
| 112 | 5 | 4 | 4 | 4 | 0 | 1 | 1 | 1 |
| 113 | 4 | 16 | 0 | 0 | 0 | 0 | 0 | 0 |
| 114 | 4 | 10 | 4 | 0 | 2 | 0 | 0 | 0 |
| 115 | 4 | 10 | 4 | 0 | 0 | 2 | 0 | 0 |
| 116 | 4 | 10 | 4 | 0 | 1 | 1 | 0 | 0 |
| 117 | 4 | 8 | 6 | 0 | 2 | 0 | 0 | 0 |
| 118 | 4 | 8 | 6 | 0 | 0 | 2 | 0 | 0 |
| 119 | 4 | 8 | 6 | 0 | 1 | 1 | 0 | 0 |
| 120 | 4 | 8 | 4 | 0 | 4 | 0 | 0 | 0 |
| 121 | 4 | 8 | 4 | 0 | 0 | 4 | 0 | 0 |
| 122 | 4 | 8 | 4 | 0 | 3 | 1 | 0 | 0 |
| 123 | 4 | 8 | 4 | 0 | 1 | 3 | 0 | 0 |
| 124 | 4 | 8 | 4 | 0 | 2 | 2 | 0 | 0 |
| 125 | 4 | 6 | 8 | 0 | 2 | 0 | 0 | 0 |
| 126 | 4 | 6 | 8 | 0 | 0 | 2 | 0 | 0 |
| 127 | 4 | 6 | 8 | 0 | 1 | 1 | 0 | 0 |
| 128 | 4 | 6 | 6 | 0 | 4 | 0 | 0 | 0 |
| 129 | 4 | 6 | 6 | 0 | 0 | 4 | 0 | 0 |
| 130 | 4 | 6 | 6 | 0 | 3 | 1 | 0 | 0 |
| 131 | 4 | 6 | 6 | 0 | 1 | 3 | 0 | 0 |
| 132 | 4 | 6 | 6 | 0 | 2 | 2 | 0 | 0 |
| 133 | 4 | 6 | 4 | 0 | 5 | 1 | 0 | 0 |
| 134 | 4 | 6 | 4 | 0 | 1 | 5 | 0 | 0 |
| 135 | 4 | 6 | 4 | 0 | 4 | 2 | 0 | 0 |
| 136 | 4 | 6 | 4 | 0 | 2 | 4 | 0 | 0 |
| 137 | 4 | 6 | 4 | 0 | 3 | 3 | 0 | 0 |
| 138 | 4 | 6 | 4 | 4 | 1 | 0 | 1 | 0 |
| 139 | 4 | 6 | 4 | 4 | 0 | 1 | 1 | 0 |
| 140 | 4 | 6 | 4 | 4 | 1 | 0 | 0 | 1 |
| 141 | 4 | 6 | 4 | 4 | 0 | 1 | 0 | 1 |
| 142 | 4 | 4 | 10 | 0 | 2 | 0 | 0 | 0 |
| 143 | 4 | 4 | 10 | 0 | 0 | 2 | 0 | 0 |
| 144 | 4 | 4 | 10 | 0 | 1 | 1 | 0 | 0 |
| 145 | 4 | 4 | 8 | 0 | 4 | 0 | 0 | 0 |
| 146 | 4 | 4 | 8 | 0 | 0 | 4 | 0 | 0 |
| 147 | 4 | 4 | 8 | 0 | 3 | 1 | 0 | 0 |
| 148 | 4 | 4 | 8 | 0 | 1 | 3 | 0 | 0 |
| 149 | 4 | 4 | 8 | 0 | 2 | 2 | 0 | 0 |
| 150 | 4 | 4 | 6 | 0 | 5 | 1 | 0 | 0 |
| 151 | 4 | 4 | 6 | 0 | 1 | 5 | 0 | 0 |
| 152 | 4 | 4 | 6 | 0 | 4 | 2 | 0 | 0 |
| 153 | 4 | 4 | 6 | 0 | 2 | 4 | 0 | 0 |
| 154 | 4 | 4 | 6 | 0 | 3 | 3 | 0 | 0 |
| 155 | 4 | 4 | 6 | 4 | 1 | 0 | 1 | 0 |
| 156 | 4 | 4 | 6 | 4 | 0 | 1 | 1 | 0 |
| 157 | 4 | 4 | 6 | 4 | 1 | 0 | 0 | 1 |
| 158 | 4 | 4 | 6 | 4 | 0 | 1 | 0 | 1 |
| 159 | 4 | 4 | 4 | 0 | 5 | 3 | 0 | 0 |
| 160 | 4 | 4 | 4 | 0 | 3 | 5 | 0 | 0 |
| 161 | 4 | 4 | 4 | 0 | 4 | 4 | 0 | 0 |
| 162 | 4 | 4 | 4 | 6 | 1 | 0 | 1 | 0 |
| 163 | 4 | 4 | 4 | 6 | 0 | 1 | 1 | 0 |
| 164 | 4 | 4 | 4 | 6 | 1 | 0 | 0 | 1 |
| 165 | 4 | 4 | 4 | 6 | 0 | 1 | 0 | 1 |
| 166 | 4 | 4 | 4 | 4 | 3 | 0 | 1 | 0 |
| 167 | 4 | 4 | 4 | 4 | 0 | 3 | 1 | 0 |
| 168 | 4 | 4 | 4 | 4 | 3 | 0 | 0 | 1 |
| 169 | 4 | 4 | 4 | 4 | 0 | 3 | 0 | 1 |
| 170 | 4 | 4 | 4 | 4 | 1 | 0 | 3 | 0 |
| 171 | 4 | 4 | 4 | 4 | 1 | 0 | 0 | 3 |
| 172 | 4 | 4 | 4 | 4 | 0 | 1 | 3 | 0 |
| 173 | 4 | 4 | 4 | 4 | 0 | 1 | 0 | 3 |
| 174 | 4 | 4 | 4 | 4 | 2 | 0 | 2 | 0 |
| 175 | 4 | 4 | 4 | 4 | 0 | 2 | 2 | 0 |
| 176 | 4 | 4 | 4 | 4 | 2 | 0 | 0 | 2 |
| 177 | 4 | 4 | 4 | 4 | 0 | 2 | 0 | 2 |
| 178 | 4 | 4 | 4 | 4 | 2 | 1 | 1 | 0 |
| 179 | 4 | 4 | 4 | 4 | 2 | 1 | 0 | 1 |
| 180 | 4 | 4 | 4 | 4 | 2 | 0 | 1 | 1 |
| 181 | 4 | 4 | 4 | 4 | 1 | 2 | 1 | 0 |
| 182 | 4 | 4 | 4 | 4 | 1 | 2 | 0 | 1 |
| 183 | 4 | 4 | 4 | 4 | 0 | 2 | 1 | 1 |
| 184 | 4 | 4 | 4 | 4 | 1 | 1 | 2 | 0 |
| 185 | 4 | 4 | 4 | 4 | 1 | 0 | 2 | 1 |
| 186 | 4 | 4 | 4 | 4 | 0 | 1 | 2 | 1 |
| 187 | 4 | 4 | 4 | 4 | 1 | 1 | 0 | 2 |
| 188 | 4 | 4 | 4 | 4 | 1 | 0 | 1 | 2 |
| 189 | 4 | 4 | 4 | 4 | 0 | 1 | 1 | 2 |
| 190 | 4 | 4 | 4 | 4 | 1 | 1 | 1 | 1 |
| 191 | 3 | 12 | 4 | 0 | 1 | 0 | 0 | 0 |
| 192 | 3 | 12 | 4 | 0 | 0 | 1 | 0 | 0 |
| 193 | 3 | 10 | 6 | 0 | 1 | 0 | 0 | 0 |
| 194 | 3 | 10 | 6 | 0 | 0 | 1 | 0 | 0 |
| 195 | 3 | 10 | 4 | 0 | 3 | 0 | 0 | 0 |
| 196 | 3 | 10 | 4 | 0 | 0 | 3 | 0 | 0 |
| 197 | 3 | 10 | 4 | 0 | 2 | 1 | 0 | 0 |
| 198 | 3 | 10 | 4 | 0 | 1 | 2 | 0 | 0 |
| 199 | 3 | 8 | 8 | 0 | 1 | 0 | 0 | 0 |
| 200 | 3 | 8 | 8 | 0 | 0 | 1 | 0 | 0 |
| 201 | 3 | 8 | 6 | 0 | 3 | 0 | 0 | 0 |
| 202 | 3 | 8 | 6 | 0 | 0 | 3 | 0 | 0 |
| 203 | 3 | 8 | 6 | 0 | 2 | 1 | 0 | 0 |
| 204 | 3 | 8 | 6 | 0 | 1 | 2 | 0 | 0 |
| 205 | 3 | 8 | 4 | 0 | 5 | 0 | 0 | 0 |
| 206 | 3 | 8 | 4 | 0 | 0 | 5 | 0 | 0 |
| 207 | 3 | 8 | 4 | 0 | 4 | 1 | 0 | 0 |
| 208 | 3 | 8 | 4 | 0 | 1 | 4 | 0 | 0 |
| 209 | 3 | 8 | 4 | 0 | 3 | 2 | 0 | 0 |
| 210 | 3 | 8 | 4 | 0 | 2 | 3 | 0 | 0 |
| 211 | 3 | 6 | 10 | 0 | 1 | 0 | 0 | 0 |
| 212 | 3 | 6 | 10 | 0 | 0 | 1 | 0 | 0 |
| 213 | 3 | 6 | 8 | 0 | 3 | 0 | 0 | 0 |
| 214 | 3 | 6 | 8 | 0 | 0 | 3 | 0 | 0 |
| 215 | 3 | 6 | 8 | 0 | 2 | 1 | 0 | 0 |
| 216 | 3 | 6 | 8 | 0 | 1 | 2 | 0 | 0 |
| 217 | 3 | 6 | 6 | 0 | 5 | 0 | 0 | 0 |
| 218 | 3 | 6 | 6 | 0 | 0 | 5 | 0 | 0 |
| 219 | 3 | 6 | 6 | 0 | 4 | 1 | 0 | 0 |
| 220 | 3 | 6 | 6 | 0 | 1 | 4 | 0 | 0 |
| 221 | 3 | 6 | 6 | 0 | 3 | 2 | 0 | 0 |
| 222 | 3 | 6 | 6 | 0 | 2 | 3 | 0 | 0 |
| 223 | 3 | 6 | 4 | 0 | 5 | 2 | 0 | 0 |
| 224 | 3 | 6 | 4 | 0 | 2 | 5 | 0 | 0 |
| 225 | 3 | 6 | 4 | 0 | 4 | 3 | 0 | 0 |
| 226 | 3 | 6 | 4 | 0 | 3 | 4 | 0 | 0 |
| 227 | 3 | 6 | 4 | 4 | 2 | 0 | 1 | 0 |
| 228 | 3 | 6 | 4 | 4 | 0 | 2 | 1 | 0 |
| 229 | 3 | 6 | 4 | 4 | 2 | 0 | 0 | 1 |

| Seq # | L | S1 | S2 | S3 | P1 | P2 | P3 | P4 |
|---|---|---|---|---|---|---|---|---|
| 230 | 3 | 6 | 4 | 4 | 0 | 2 | 0 | 1 |
| 231 | 3 | 6 | 4 | 4 | 1 | 0 | 2 | 0 |
| 232 | 3 | 6 | 4 | 4 | 0 | 1 | 2 | 0 |
| 233 | 3 | 6 | 4 | 4 | 1 | 0 | 0 | 2 |
| 234 | 3 | 6 | 4 | 4 | 0 | 1 | 0 | 2 |
| 235 | 3 | 6 | 4 | 4 | 1 | 1 | 1 | 0 |
| 236 | 3 | 6 | 4 | 4 | 1 | 1 | 0 | 1 |
| 237 | 3 | 6 | 4 | 4 | 1 | 0 | 1 | 1 |
| 238 | 3 | 6 | 4 | 4 | 0 | 1 | 1 | 1 |
| 239 | 3 | 4 | 12 | 0 | 1 | 0 | 0 | 0 |
| 240 | 3 | 4 | 12 | 0 | 0 | 1 | 0 | 0 |
| 241 | 3 | 4 | 10 | 0 | 3 | 0 | 0 | 0 |
| 242 | 3 | 4 | 10 | 0 | 0 | 3 | 0 | 0 |
| 243 | 3 | 4 | 10 | 0 | 2 | 1 | 0 | 0 |
| 244 | 3 | 4 | 10 | 0 | 1 | 2 | 0 | 0 |
| 245 | 3 | 4 | 8 | 0 | 5 | 0 | 0 | 0 |
| 246 | 3 | 4 | 8 | 0 | 0 | 5 | 0 | 0 |
| 247 | 3 | 4 | 8 | 0 | 4 | 1 | 0 | 0 |
| 248 | 3 | 4 | 8 | 0 | 1 | 4 | 0 | 0 |
| 249 | 3 | 4 | 8 | 0 | 3 | 2 | 0 | 0 |
| 250 | 3 | 4 | 8 | 0 | 2 | 3 | 0 | 0 |
| 251 | 3 | 4 | 6 | 0 | 5 | 2 | 0 | 0 |
| 252 | 3 | 4 | 6 | 0 | 2 | 5 | 0 | 0 |
| 253 | 3 | 4 | 6 | 0 | 4 | 3 | 0 | 0 |
| 254 | 3 | 4 | 6 | 0 | 3 | 4 | 0 | 0 |
| 255 | 3 | 4 | 6 | 4 | 2 | 0 | 1 | 0 |
| 256 | 3 | 4 | 6 | 4 | 0 | 2 | 1 | 0 |
| 257 | 3 | 4 | 6 | 4 | 2 | 0 | 0 | 1 |
| 258 | 3 | 4 | 6 | 4 | 0 | 2 | 0 | 1 |
| 259 | 3 | 4 | 6 | 4 | 1 | 0 | 2 | 0 |
| 260 | 3 | 4 | 6 | 4 | 0 | 1 | 2 | 0 |
| 261 | 3 | 4 | 6 | 4 | 1 | 0 | 0 | 2 |
| 262 | 3 | 4 | 6 | 4 | 0 | 1 | 0 | 2 |
| 263 | 3 | 4 | 6 | 4 | 1 | 1 | 1 | 0 |
| 264 | 3 | 4 | 6 | 4 | 1 | 1 | 0 | 1 |
| 265 | 3 | 4 | 6 | 4 | 1 | 0 | 1 | 1 |
| 266 | 3 | 4 | 6 | 4 | 0 | 1 | 1 | 1 |
| 267 | 3 | 4 | 4 | 0 | 5 | 4 | 0 | 0 |
| 268 | 3 | 4 | 4 | 0 | 4 | 5 | 0 | 0 |
| 269 | 3 | 4 | 4 | 6 | 2 | 0 | 1 | 0 |
| 270 | 3 | 4 | 4 | 6 | 0 | 2 | 1 | 0 |
| 271 | 3 | 4 | 4 | 6 | 2 | 0 | 0 | 1 |
| 272 | 3 | 4 | 4 | 6 | 0 | 2 | 0 | 1 |
| 273 | 3 | 4 | 4 | 6 | 1 | 0 | 2 | 0 |
| 274 | 3 | 4 | 4 | 6 | 0 | 1 | 2 | 0 |
| 275 | 3 | 4 | 4 | 6 | 1 | 0 | 0 | 2 |
| 276 | 3 | 4 | 4 | 6 | 0 | 1 | 0 | 2 |
| 277 | 3 | 4 | 4 | 6 | 1 | 1 | 1 | 0 |
| 278 | 3 | 4 | 4 | 6 | 1 | 1 | 0 | 1 |
| 279 | 3 | 4 | 4 | 6 | 1 | 0 | 1 | 1 |
| 280 | 3 | 4 | 4 | 6 | 0 | 1 | 1 | 1 |
| 281 | 3 | 4 | 4 | 4 | 4 | 0 | 1 | 0 |
| 282 | 3 | 4 | 4 | 4 | 0 | 4 | 1 | 0 |
| 283 | 3 | 4 | 4 | 4 | 4 | 0 | 0 | 1 |
| 284 | 3 | 4 | 4 | 4 | 0 | 4 | 0 | 1 |
| 285 | 3 | 4 | 4 | 4 | 1 | 0 | 4 | 0 |
| 286 | 3 | 4 | 4 | 4 | 1 | 0 | 0 | 4 |
| 287 | 3 | 4 | 4 | 4 | 0 | 1 | 4 | 0 |
| 288 | 3 | 4 | 4 | 4 | 0 | 1 | 0 | 4 |
| 289 | 3 | 4 | 4 | 4 | 3 | 0 | 2 | 0 |
| 290 | 3 | 4 | 4 | 4 | 0 | 3 | 2 | 0 |
| 291 | 3 | 4 | 4 | 4 | 3 | 0 | 0 | 2 |
| 292 | 3 | 4 | 4 | 4 | 0 | 3 | 0 | 2 |
| 293 | 3 | 4 | 4 | 4 | 2 | 0 | 3 | 0 |
| 294 | 3 | 4 | 4 | 4 | 2 | 0 | 0 | 3 |
| 295 | 3 | 4 | 4 | 4 | 0 | 2 | 3 | 0 |
| 296 | 3 | 4 | 4 | 4 | 0 | 2 | 0 | 3 |
| 297 | 3 | 4 | 4 | 4 | 3 | 0 | 1 | 1 |
| 298 | 3 | 4 | 4 | 4 | 3 | 1 | 0 | 1 |
| 299 | 3 | 4 | 4 | 4 | 3 | 1 | 1 | 0 |
| 300 | 3 | 4 | 4 | 4 | 0 | 3 | 1 | 1 |
| 301 | 3 | 4 | 4 | 4 | 1 | 3 | 0 | 1 |
| 302 | 3 | 4 | 4 | 4 | 1 | 3 | 1 | 0 |
| 303 | 3 | 4 | 4 | 4 | 1 | 1 | 3 | 0 |
| 304 | 3 | 4 | 4 | 4 | 0 | 1 | 3 | 1 |
| 305 | 3 | 4 | 4 | 4 | 1 | 0 | 3 | 1 |
| 306 | 3 | 4 | 4 | 4 | 1 | 1 | 0 | 3 |
| 307 | 3 | 4 | 4 | 4 | 1 | 0 | 1 | 3 |
| 308 | 3 | 4 | 4 | 4 | 0 | 1 | 1 | 3 |
| 309 | 3 | 4 | 4 | 4 | 2 | 2 | 1 | 0 |
| 310 | 3 | 4 | 4 | 4 | 2 | 2 | 0 | 1 |
| 311 | 3 | 4 | 4 | 4 | 1 | 0 | 2 | 2 |
| 312 | 3 | 4 | 4 | 4 | 0 | 1 | 2 | 2 |
| 313 | 3 | 4 | 4 | 4 | 2 | 1 | 2 | 0 |
| 314 | 3 | 4 | 4 | 4 | 2 | 1 | 0 | 2 |
| 315 | 3 | 4 | 4 | 4 | 2 | 0 | 2 | 1 |
| 316 | 3 | 4 | 4 | 4 | 0 | 2 | 2 | 1 |
| 317 | 3 | 4 | 4 | 4 | 1 | 2 | 2 | 0 |
| 318 | 3 | 4 | 4 | 4 | 1 | 2 | 0 | 2 |
| 319 | 3 | 4 | 4 | 4 | 2 | 0 | 1 | 2 |
| 320 | 3 | 4 | 4 | 4 | 0 | 2 | 1 | 2 |
| 321 | 3 | 4 | 4 | 4 | 2 | 1 | 1 | 1 |
| 322 | 3 | 4 | 4 | 4 | 1 | 2 | 1 | 1 |
| 323 | 3 | 4 | 4 | 4 | 1 | 1 | 2 | 1 |
| 324 | 3 | 4 | 4 | 4 | 1 | 1 | 1 | 2 |

Example II

Example of Further Enrichment

Figure 4:
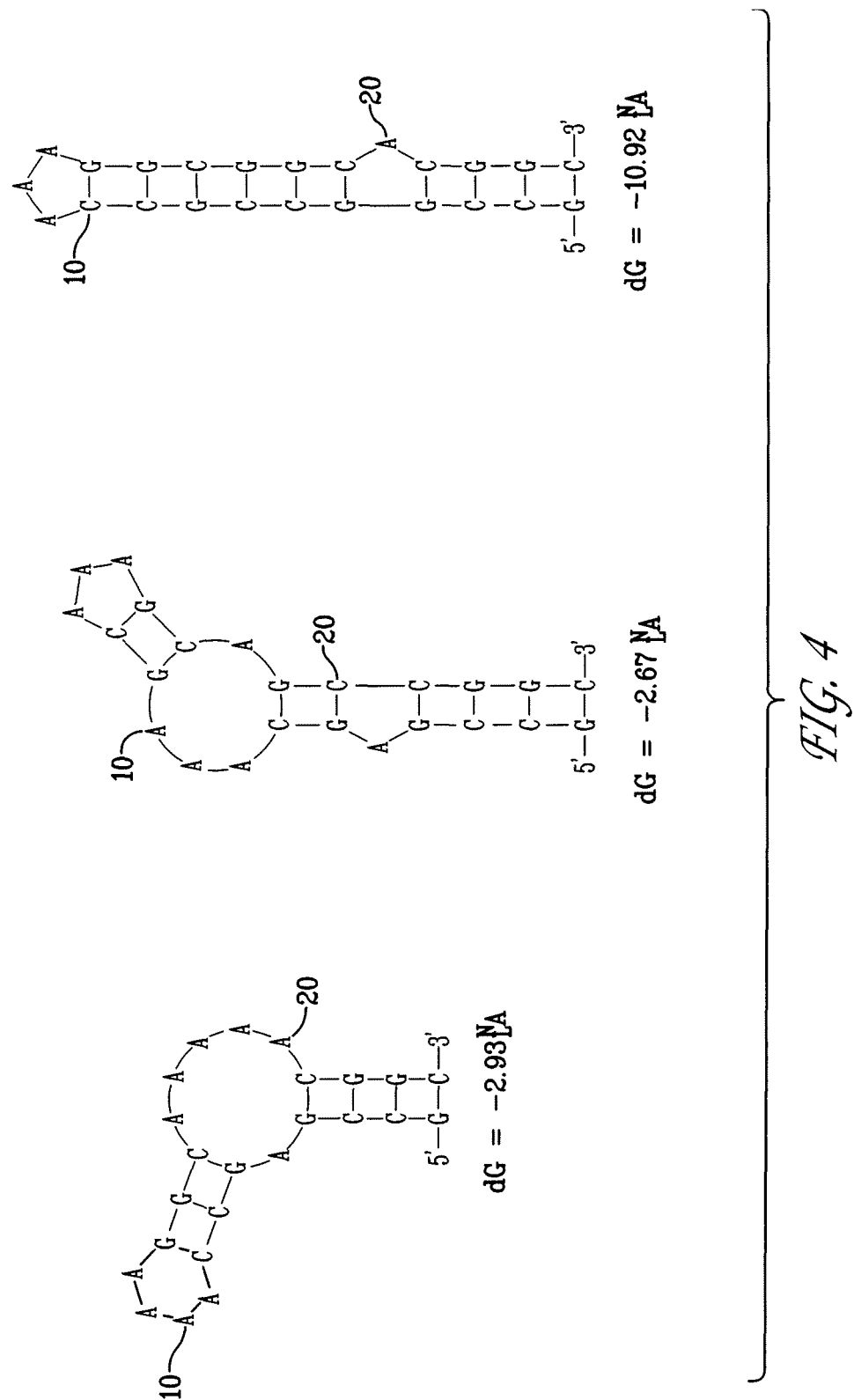
FIG. 4 depicts an example of aptamer geometries where there are only a limited number of unique, stable aptamer geometries, which may be characterized by GC rich stems.

In an exemplary embodiment of further enrichment, statistical measures governing existing aptamers are applied. High GC content is used in the stems to create the most stable aptamer geometries. In order to avoid alternate geometries to those intended, low GC content is used in the loops and pockets. In an exemplary embodiment, arbitrary sequences according to the above guidelines were chosen to form the stem, loop and pocket regions as follows: GCCGC-CGCCG (for use in the stem) and AAAAAAAAAAAAAA (for use in pockets and loops). Only the number of bases designated in the spreadsheet in Example I were selected from the forgoing sequences. Examples of these geometries are shown in FIG. 4. Since all the unique geometries are represented and the stems are in their most stable form with high GC content, and the loop and pocket variability is limited to AT rich sequences, the starting content has been greatly enriched. In an exemplary embodiment, four extra bases were added to the beginning of stem 1 in order to increase the number of geometries that assumed the predicted form. Exemplary sequences are listed in the following table and are correlated with the table in Example I for all possible geometries of a 20mer, where each column heading has the same meaning as defined in Example I:

| SEQ ID NO | S1 | P1 | S2 | P3 | S3 | L | S3 | P4 | S2 | P2 | S1 |
|---|---|---|---|---|---|---|---|---|---|---|---|
| 1 | GCCGCCG | | | | | AAAAAAAAAA | | | | | CGGCGGC |
| 2 | GCCGC | A | GC | | | AAAAAAAA | | GC | | | GCGGC |

| SEQ ID NO | S1 | P1 | S2 | P3 | S3 | L | S3 | P4 | S2 | P2 | S1 |
|---|---|---|---|---|---|---|---|---|---|---|---|
| 3 | GCCGC | | GC | | | AAAAAAAA | | | GC | A | GCGGC |
| 4 | GCCG | A | GCC | | | AAAAAAAA | | | GGC | | CGGC |
| 5 | GCCG | | GCC | | | AAAAAAAA | | | GGC | A | CGGC |
| 6 | GCCG | AAA | GC | | | AAAAAAAA | | | GC | | CGGC |
| 7 | GCCG | | GC | | | AAAAAAAA | | | GC | AAA | CGGC |
| 8 | GCCG | AA | GC | | | AAAAAAAA | | | GC | A | CGGC |
| 9 | GCCG | A | GC | | | AAAAAAAA | | | GC | AA | CGGC |
| 10 | GCCGCCGC | | | | | AAAAAAAA | | | | | GCGGCGGC |
| 11 | GCCGC | AA | GC | | | AAAAAAA | | | GC | | GCGGC |
| 12 | GCCGC | | GC | | | AAAAAAA | | | GC | AA | GCGGC |
| 13 | GCCGC | A | GC | | | AAAAAAA | | | GC | A | GCGGC |
| 14 | GCCG | AA | GCC | | | AAAAAAA | | | GGC | | CGGC |
| 15 | GCCG | | GCC | | | AAAAAAA | | | GGC | AA | CGGC |
| 16 | GCCG | A | GCC | | | AAAAAAA | | | GGC | A | CGGC |
| 17 | GCCG | AAAA | GC | | | AAAAAAA | | | GC | | CGGC |
| 18 | GCCG | | GC | | | AAAAAAA | | | GC | AAAA | CGGC |
| 19 | GCCG | AAA | GC | | | AAAAAAA | | | GC | A | CGGC |
| 20 | GCCG | A | GC | | | AAAAAAA | | | GC | AAA | CGGC |
| 21 | GCCG | AA | GC | | | AAAAAAA | | | GC | AA | CGGC |
| 22 | GCCGCC | A | GC | | | AAAAAAA | | | GC | | GGCGGC |
| 23 | GCCGCC | | GC | | | AAAAAAA | | | GC | A | GGCGGC |
| 24 | GCCGC | A | GCC | | | AAAAAAA | | | GGC | | GCGGC |
| 25 | GCCGC | | GCC | | | AAAAAAA | | | GGC | A | GCGGC |
| 26 | GCCGC | AAA | GC | | | AAAAAAA | | | GC | | GCGGC |
| 27 | GCCGC | | GC | | | AAAAAAA | | | GC | AAA | GCGGC |
| 28 | GCCGC | AA | GC | | | AAAAAAA | | | GC | A | GCGGC |
| 29 | GCCGC | A | GC | | | AAAAAAA | | | GC | AA | GCGGC |
| 30 | GCCG | A | GCCG | | | AAAAAAA | | | CGGC | | CGGC |
| 31 | GCCG | | GCCG | | | AAAAAAA | | | CGGC | A | CGGC |
| 32 | GCCG | AAA | GCC | | | AAAAAAA | | | GGC | | CGGC |
| 33 | GCCG | | GCC | | | AAAAAAA | | | GGC | AAA | CGGC |
| 34 | GCCG | AA | GCC | | | AAAAAAA | | | GGC | A | CGGC |
| 35 | GCCG | A | GCC | | | AAAAAAA | | | GGC | AA | CGGC |
| 36 | GCCG | AAAAA | GC | | | AAAAAAA | | | GC | | CGGC |
| 37 | GCCG | | GC | | | AAAAAAA | | | GC | AAAAA | CGGC |
| 38 | GCCG | AAAA | GC | | | AAAAAAA | | | GC | A | CGGC |
| 39 | GCCG | A | GC | | | AAAAAAA | | | GC | AAAA | CGGC |
| 40 | GCCG | AAA | GC | | | AAAAAAA | | | GC | AA | CGGC |

-continued

| SEQ ID NO | S1 | P1 | S2 | P3 | S3 | L | S3 | P4 | S2 | P2 | S1 |
|---|---|---|---|---|---|---|---|---|---|---|---|
| 41 | GCCG | AA | GC | | | AAAAAA | | | GC | AAA | CGGC |
| 42 | GCCGCCGCC | | | | | AAAAAA | | | | | GGCGGCGGC |
| 43 | GCCGCC | AA | GC | | | AAAAAA | | | GC | | GGCGGC |
| 44 | GCCGCC | | GC | | | AAAAAA | | | GC | AA | GGCGGC |
| 45 | GCCGCC | A | GC | | | AAAAAA | | | GC | A | GGCGGC |
| 46 | GCCGC | AA | GCC | | | AAAAAA | | | GGC | | GCGGC |
| 47 | GCCGC | | GCC | | | AAAAAA | | | GGC | AA | GCGGC |
| 48 | GCCGC | A | GCC | | | AAAAAA | | | GGC | A | GCGGC |
| 49 | GCCGC | AAAA | GC | | | AAAAAA | | | GC | | GCGGC |
| 50 | GCCGC | | GC | | | AAAAAA | | | GC | AAAA | GCGGC |
| 51 | GCCGC | AAA | GC | | | AAAAAA | | | GC | A | GCGGC |
| 52 | GCCGC | A | GC | | | AAAAAA | | | GC | AAA | GCGGC |
| 53 | GCCGC | AA | GC | | | AAAAAA | | | GC | AA | GCGGC |
| 54 | GCCG | AA | GCCG | | | AAAAAA | | | CGGC | | CGGC |
| 55 | GCCG | | GCCG | | | AAAAAA | | | CGGC | AA | CGGC |
| 56 | GCCG | A | GCCG | | | AAAAAA | | | CGGC | A | CGGC |
| 57 | GCCG | AAAA | GCC | | | AAAAAA | | | GGC | | CGGC |
| 58 | GCCG | | GCC | | | AAAAAA | | | GGC | AAAA | CGGC |
| 59 | GCCG | AAA | GCC | | | AAAAAA | | | GGC | A | CGGC |
| 60 | GCCG | A | GCC | | | AAAAAA | | | GGC | AAA | CGGC |
| 61 | GCCG | AA | GCC | | | AAAAAA | | | GGC | AA | CGGC |
| 62 | GCCG | AAAAA | GC | | | AAAAAA | | | GC | A | CGGC |
| 63 | GCCG | A | GC | | | AAAAAA | | | GC | AAAAA | CGGC |
| 64 | GCCG | AAAA | GC | | | AAAAAA | | | GC | AA | CGGC |
| 65 | GCCG | AA | GC | | | AAAAAA | | | GC | AAAA | CGGC |
| 66 | GCCG | AAA | GC | | | AAAAAA | | | GC | AAA | CGGC |
| 67 | GCCG | A | GC | A | GC | AAAAAA | GC | | GC | | CGGC |
| 68 | GCCG | | GC | A | GC | AAAAAA | GC | | GC | A | CGGC |
| 69 | GCCG | A | GC | | GC | AAAAAA | GC | A | GC | | CGGC |
| 70 | GCCG | | GC | | GC | AAAAAA | GC | A | GC | A | CGGC |
| 71 | GCCGCC | A | GCC | | | AAAAA | | | GGC | | GGCGGC |
| 72 | GCCGCC | | GCC | | | AAAAA | | | GGC | A | GGCGGC |
| 73 | GCCGCC | AAA | GC | | | AAAAA | | | GC | | GGCGGC |
| 74 | GCCGCC | | GC | | | AAAAA | | | GC | AAA | GGCGGC |
| 75 | GCCGCC | AA | GC | | | AAAAA | | | GC | A | GGCGGC |
| 76 | GCCGCC | A | GC | | | AAAAA | | | GC | AA | GGCGGC |
| 77 | GCCGC | A | GCCG | | | AAAAA | | | CGGC | | GCGGC |
| 78 | GCCGC | | GCCG | | | AAAAA | | | CGGC | A | GCGGC |

-continued

| SEQ ID NO | S1 | P1 | S2 | P3 | S3 | L | S3 | P4 | S2 | P2 | S1 |
|---|---|---|---|---|---|---|---|---|---|---|---|
| 79 | GCCGC | AAA | GCC | | | AAAAA | | | GGC | | GCGGC |
| 80 | GCCGC | | GCC | | | AAAAA | | | GGC | AAA | GCGGC |
| 81 | GCCGC | AA | GCC | | | AAAAA | | | GGC | A | GCGGC |
| 82 | GCCGC | A | GCC | | | AAAAA | | | GGC | AA | GCGGC |
| 83 | GCCGC | AAAAA | GC | | | AAAAA | | | GC | | GCGGC |
| 84 | GCCGC | | GC | | | AAAAA | | | GC | AAAAA | GCGGC |
| 85 | GCCGC | AAAA | GC | | | AAAAA | | | GC | A | GCGGC |
| 86 | GCCGC | A | GC | | | AAAAA | | | GC | AAAA | GCGGC |
| 87 | GCCGC | AAA | GC | | | AAAAA | | | GC | AA | GCGGC |
| 88 | GCCGC | AA | GC | | | AAAAA | | | GC | AAA | GCGGC |
| 89 | GCCG | A | GCCGC | | | AAAAA | | | GCGGC | | CGGC |
| 90 | GCCG | | GCCGC | | | AAAAA | | | GCGGC | A | CGGC |
| 91 | GCCG | AAA | GCCG | | | AAAAA | | | CGGC | | CGGC |
| 92 | GCCG | | GCCG | | | AAAAA | | | CGGC | AAA | CGGC |
| 93 | GCCG | AA | GCCG | | | AAAAA | | | CGGC | A | CGGC |
| 94 | GCCG | A | GCCG | | | AAAAA | | | CGGC | AA | CGGC |
| 95 | GCCG | AAAAA | GCC | | | AAAAA | | | GGC | | CGGC |
| 96 | GCCG | | GCC | | | AAAAA | | | GGC | AAAAA | CGGC |
| 97 | GCCG | AAAA | GCC | | | AAAAA | | | GGC | A | CGGC |
| 98 | GCCG | A | GCC | | | AAAAA | | | GGC | AAAA | CGGC |
| 99 | GCCG | AAA | GCC | | | AAAAA | | | GGC | AA | CGGC |
| 100 | GCCG | AA | GCC | | | AAAAA | | | GGC | AAA | CGGC |
| 101 | GCCG | AA | GC | A | GC | AAAAA | GC | | GC | | CGGC |
| 102 | GCCG | | GC | A | GC | AAAAA | GC | | GC | AA | CGGC |
| 103 | GCCG | AA | GC | | GC | AAAAA | GC | A | GC | | CGGC |
| 104 | GCCG | | GC | | GC | AAAAA | GC | A | GC | AA | CGGC |
| 105 | GCCG | A | GC | AA | GC | AAAAA | GC | | GC | | CGGC |
| 106 | GCCG | | GC | AA | GC | AAAAA | GC | | GC | A | CGGC |
| 107 | GCCG | A | GC | | GC | AAAAA | GC | AA | GC | | CGGC |
| 108 | GCCG | | GC | | GC | AAAAA | GC | AA | GC | A | CGGC |
| 109 | GCCG | A | GC | A | GC | AAAAA | GC | | GC | A | CGGC |
| 110 | GCCG | A | GC | | GC | AAAAA | GC | A | GC | A | CGGC |
| 111 | GCCG | A | GC | A | GC | AAAAA | GC | A | GC | | CGGC |
| 112 | GCCG | | GC | A | GC | AAAAA | GC | A | GC | A | CGGC |
| 113 | GCCGCCGCCG | | | | | AAAA | | | | | CGGCGGCGGC |
| 114 | GCCGCCG | AA | GC | | | AAAA | | | GC | | CGGCGGC |
| 115 | GCCGCCG | | GC | | | AAAA | | | GC | AA | CGGCGGC |
| 116 | GCCGCCG | A | GC | | | AAAA | | | GC | A | CGGCGGC |

-continued

| SEQ ID NO | S1 | P1 | S2 | P3 | S3 | L | S3 | P4 | S2 | P2 | S1 |
|---|---|---|---|---|---|---|---|---|---|---|---|
| 117 | GCCGCC | AA | GCC | | | AAAA | | | GGC | | GGCGGC |
| 118 | GCCGCC | | GCC | | | AAAA | | | GGC | AA | GGCGGC |
| 119 | GCCGCC | A | GCC | | | AAAA | | | GGC | A | GGCGGC |
| 120 | GCCGCC | AAAA | GC | | | AAAA | | | GC | | GGCGGC |
| 121 | GCCGCC | | GC | | | AAAA | | | GC | AAAA | GGCGGC |
| 122 | GCCGCC | AAA | GC | | | AAAA | | | GC | A | GGCGGC |
| 123 | GCCGCC | A | GC | | | AAAA | | | GC | AAA | GGCGGC |
| 124 | GCCGCC | AA | GC | | | AAAA | | | GC | AA | GGCGGC |
| 125 | GCCGC | AA | GCCG | | | AAAA | | | CGGC | | GCGGC |
| 126 | GCCGC | | GCCG | | | AAAA | | | CGGC | AA | GCGGC |
| 127 | GCCGC | A | GCCG | | | AAAA | | | CGGC | A | GCGGC |
| 128 | GCCGC | AAAA | GCC | | | AAAA | | | GGC | | GCGGC |
| 129 | GCCGC | | GCC | | | AAAA | | | GGC | AAAA | GCGGC |
| 130 | GCCGC | AAA | GCC | | | AAAA | | | GGC | A | GCGGC |
| 131 | GCCGC | A | GCC | | | AAAA | | | GGC | AAA | GCGGC |
| 132 | GCCGC | AA | GCC | | | AAAA | | | GGC | AA | GCGGC |
| 133 | GCCGC | AAAAA | GC | | | AAAA | | | GC | A | GCGGC |
| 134 | GCCGC | A | GC | | | AAAA | | | GC | AAAAA | GCGGC |
| 135 | GCCGC | AAAA | GC | | | AAAA | | | GC | AA | GCGGC |
| 136 | GCCGC | AA | GC | | | AAAA | | | GC | AAAA | GCGGC |
| 137 | GCCGC | AAA | GC | | | AAAA | | | GC | AAA | GCGGC |
| 138 | GCCGC | A | GC | A | GC | AAAA | GC | | GC | | GCGGC |
| 139 | GCCGC | | GC | A | GC | AAAA | GC | | GC | A | GCGGC |
| 140 | GCCGC | A | GC | | GC | AAAA | GC | A | GC | | GCGGC |
| 141 | GCCGC | | GC | | GC | AAAA | GC | A | GC | A | GCGGC |
| 142 | GCCG | AA | GCCGC | | | AAAA | | | GCGGC | | CGGC |
| 143 | GCCG | | GCCGC | | | AAAA | | | GCGGC | AA | CGGC |
| 144 | GCCG | A | GCCGC | | | AAAA | | | GCGGC | A | CGGC |
| 145 | GCCG | AAAA | GCCG | | | AAAA | | | CGGC | | CGGC |
| 146 | GCCG | | GCCG | | | AAAA | | | CGGC | AAAA | CGGC |
| 147 | GCCG | AAA | GCCG | | | AAAA | | | CGGC | A | CGGC |
| 148 | GCCG | A | GCCG | | | AAAA | | | CGGC | AAA | CGGC |
| 149 | GCCG | AA | GCCG | | | AAAA | | | CGGC | AA | CGGC |
| 150 | GCCG | AAAAA | GCC | | | AAAA | | | GGC | A | CGGC |
| 151 | GCCG | A | GCC | | | AAAA | | | GGC | AAAAA | CGGC |
| 152 | GCCG | AAAA | GCC | | | AAAA | | | GGC | AA | CGGC |
| 153 | GCCG | AA | GCC | | | AAAA | | | GGC | AAAA | CGGC |
| 154 | GCCG | AAA | GCC | | | AAAA | | | GGC | AAA | CGGC |

-continued

| SEQ ID NO S1 | P1 | S2 | P3 | S3 | L | S3 | P4 | S2 | P2 | S1 |
|---|---|---|---|---|---|---|---|---|---|---|
| 155 GCCG | A | GCC | A | GC | AAAA | GC |  | GGC |  | CGGC |
| 156 GCCG |  | GCC | A | GC | AAAA | GC |  | GGC | A | CGGC |
| 157 GCCG | A | GCC |  | GC | AAAA | GC | A | GGC |  | CGGC |
| 158 GCCG |  | GCC |  | GC | AAAA | GC | A | GGC | A | CGGC |
| 159 GCCG | AAAAA | GC |  |  | AAAA |  |  | GC | AAA | CGGC |
| 160 GCCG | AAA | GC |  |  | AAAA |  |  | GC | AAAAA | CGGC |
| 161 GCCG | AAAA | GC |  |  | AAAA |  |  | GC | AAAA | CGGC |
| 162 GCCG | A | GC | A | GCC | AAAA | GGC |  | GC |  | CGGC |
| 163 GCCG |  | GC | A | GCC | AAAA | GGC |  | GC | A | CGGC |
| 164 GCCG | A | GC |  | GCC | AAAA | GGC | A | GC |  | CGGC |
| 165 GCCG |  | GC |  | GCC | AAAA | GGC | A | GC | A | CGGC |
| 166 GCCG | AAA | GC | A | GC | AAAA | GC |  | GC |  | CGGC |
| 167 GCCG |  | GC | A | GC | AAAA | GC |  | GC | AAA | CGGC |
| 168 GCCG | AAA | GC |  | GC | AAAA | GC | A | GC |  | CGGC |
| 169 GCCG |  | GC |  | GC | AAAA | GC | A | GC | AAA | CGGC |
| 170 GCCG | A | GC | AAA | GC | AAAA | GC |  | GC |  | CGGC |
| 171 GCCG | A | GC |  | GC | AAAA | GC | AAA | GC |  | CGGC |
| 172 GCCG |  | GC | AAA | GC | AAAA | GC |  | GC | A | CGGC |
| 173 GCCG |  | GC |  | GC | AAAA | GC | AAA | GC | A | CGGC |
| 174 GCCG | AA | GC | AA | GC | AAAA | GC |  | GC |  | CGGC |
| 175 GCCG |  | GC | AA | GC | AAAA | GC |  | GC | AA | CGGC |
| 176 GCCG | AA | GC |  | GC | AAAA | GC | AA | GC |  | CGGC |
| 177 GCCG |  | GC |  | GC | AAAA | GC | AA | GC | AA | CGGC |
| 178 GCCG | AA | GC | A | GC | AAAA | GC |  | GC | A | CGGC |
| 179 GCCG | AA | GC |  | GC | AAAA | GC | A | GC | A | CGGC |
| 180 GCCG | AA | GC | A | GC | AAAA | GC | A | GC |  | CGGC |
| 181 GCCG | A | GC | A | GC | AAAA | GC | GC | AA | CGGC |  |
| 182 GCCG | A | GC |  | GC | AAAA | GC | A | GC | AA | CGGC |
| 183 GCCG |  | GC | A | GC | AAAA | GC | A | GC | AA | CGGC |
| 184 GCCG | A | GC | AA | GC | AAAA | GC |  | GC | A | CGGC |
| 185 GCCG | A | GC | AA | GC | AAAA | GC | A | GC |  | CGGC |
| 186 GCCG |  | GC | AA | GC | AAAA | GC | A | GC | A | CGGC |
| 187 GCCG | A | GC |  | GC | AAAA | GC | AA | GC | A | CGGC |
| 188 GCCG | A | GC | A | GC | AAAA | GC | AA | GC |  | CGGC |
| 189 GCCG |  | GC | A | GC | AAAA | GC | AA | GC | A | CGGC |
| 190 GCCG | A | GC | A | GC | AAAA | GC | A | GC | A | CGGC |
| 191 GCCGCCGC | A | GC |  |  | AAA |  |  | GC |  | GCGGCGGC |
| 192 GCCGCCGC |  | GC |  |  | AAA |  |  | GC | A | GCGGCGGC |

-continued

| SEQ ID NO | S1 | P1 | S2 | P3 | S3 | L | S3 | P4 | S2 | P2 | S1 |
|---|---|---|---|---|---|---|---|---|---|---|---|
| 193 | GCCGCCG | A | GCC | | | AAA | | | GGC | | CGGCGGC |
| 194 | GCCGCCG | | GCC | | | AAA | | | GGC | A | CGGCGGC |
| 195 | GCCGCCG | AAA | GC | | | AAA | | | GC | | CGGCGGC |
| 196 | GCCGCCG | | GC | | | AAA | | | GC | AAA | CGGCGGC |
| 197 | GCCGCCG | AA | GC | | | AAA | | | GC | A | CGGCGGC |
| 198 | GCCGCCG | A | GC | | | AAA | | | GC | AA | CGGCGGC |
| 199 | GCCGCC | A | GCCG | | | AAA | | | CGGC | | GGCGGC |
| 200 | GCCGCC | | GCCG | | | AAA | | | CGGC | A | GGCGGC |
| 201 | GCCGCC | AAA | GCC | | | AAA | | | GGC | | GGCGGC |
| 202 | GCCGCC | | GCC | | | AAA | | | GGC | AAA | GGCGGC |
| 203 | GCCGCC | AA | GCC | | | AAA | | | GGC | A | GGCGGC |
| 204 | GCCGCC | A | GCC | | | AAA | | | GGC | AA | GGCGGC |
| 205 | GCCGCC | AAAAA | GC | | | AAA | | | GC | | GGCGGC |
| 206 | GCCGCC | | GC | | | AAA | | | GC | AAAAA | GGCGGC |
| 207 | GCCGCC | AAAA | GC | | | AAA | | | GC | A | GGCGGC |
| 208 | GCCGCC | A | GC | | | AAA | | | GC | AAAA | GGCGGC |
| 209 | GCCGCC | AAA | GC | | | AAA | | | GC | AA | GGCGGC |
| 210 | GCCGCC | AA | GC | | | AAA | | | GC | AAA | GGCGGC |
| 211 | GCCGC | A | GCCGC | | | AAA | | | GCGGC | | GCGGC |
| 212 | GCCGC | | GCCGC | | | AAA | | | GCGGC | A | GCGGC |
| 213 | GCCGC | AAA | GCCG | | | AAA | | | CGGC | | GCGGC |
| 214 | GCCGC | | GCCG | | | AAA | | | CGGC | AAA | GCGGC |
| 215 | GCCGC | AA | GCCG | | | AAA | | | CGGC | A | GCGGC |
| 216 | GCCGC | A | GCCG | | | AAA | | | CGGC | AA | GCGGC |
| 217 | GCCGC | AAAAA | GCC | | | AAA | | | GGC | | GCGGC |
| 218 | GCCGC | | GCC | | | AAA | | | GGC | AAAAA | GCGGC |
| 219 | GCCGC | AAAA | GCC | | | AAA | | | GGC | A | GCGGC |
| 220 | GCCGC | A | GCC | | | AAA | | | GGC | AAAA | GCGGC |
| 221 | GCCGC | AAA | GCC | | | AAA | | | GGC | AA | GCGGC |
| 222 | GCCGC | AA | GCC | | | AAA | | | GGC | AAA | GCGGC |
| 223 | GCCGC | AAAAA | GC | | | AAA | | | GC | AA | GCGGC |
| 224 | GCCGC | AA | GC | | | AAA | | | GC | AAAAA | GCGGC |
| 225 | GCCGC | AAAA | GC | | | AAA | | | GC | AAA | GCGGC |
| 226 | GCCGC | AAA | GC | | | AAA | | | GC | AAAA | GCGGC |
| 227 | GCCGC | AA | GC | A | GC | AAA | GC | | GC | | GCGGC |
| 228 | GCCGC | | GC | A | GC | AAA | GC | | GC | AA | GCGGC |
| 229 | GCCGC | AA | GC | | GC | AAA | GC | A | GC | | GCGGC |
| 230 | GCCGC | | GC | | GC | AAA | GC | A | GC | AA | GCGGC |

-continued

| SEQ ID NO | S1 | P1 | S2 | P3 | S3 | L | S3 | P4 | S2 | P2 | S1 |
|---|---|---|---|---|---|---|---|---|---|---|---|
| 231 | GCCGC | A | GC | AA | GC | AAA | GC | | GC | | GCGGC |
| 232 | GCCGC | | GC | AA | GC | AAA | GC | | GC | A | GCGGC |
| 233 | GCCGC | A | GC | | GC | AAA | GC | AA | GC | | GCGGC |
| 234 | GCCGC | | GC | | GC | AAA | GC | AA | GC | A | GCGGC |
| 235 | GCCGC | A | GC | A | GC | AAA | GC | | GC | A | GCGGC |
| 236 | GCCGC | A | GC | | GC | AAA | GC | A | GC | A | GCGGC |
| 237 | GCCGC | A | GC | A | GC | AAA | GC | A | GC | | GCGGC |
| 238 | GCCGC | | GC | A | GC | AAA | GC | A | GC | A | GCGGC |
| 239 | GCCG | A | GCCGCC | | | AAA | | | GGCGGC | | CGGC |
| 240 | GCCG | | GCCGCC | | | AAA | | | GGCGGC | A | CGGC |
| 241 | GCCG | AAA | GCCGC | | | AAA | | | GCGGC | | CGGC |
| 242 | GCCG | | GCCGC | | | AAA | | | GCGGC | AAA | CGGC |
| 243 | GCCG | AA | GCCGC | | | AAA | | | GCGGC | A | CGGC |
| 244 | GCCG | A | GCCGC | | | AAA | | | GCGGC | AA | CGGC |
| 245 | GCCG | AAAAA | GCCG | | | AAA | | | CGGC | | CGGC |
| 246 | GCCG | | GCCG | | | AAA | | | CGGC | AAAAA | CGGC |
| 247 | GCCG | AAAA | GCCG | | | AAA | | | CGGC | A | CGGC |
| 248 | GCCG | A | GCCG | | | AAA | | | CGGC | AAAA | CGGC |
| 249 | GCCG | AAA | GCCG | | | AAA | | | CGGC | AA | CGGC |
| 250 | GCCG | AA | GCCG | | | AAA | | | CGGC | AAA | CGGC |
| 251 | GCCG | AAAAA | GCC | | | AAA | | | GGC | AA | CGGC |
| 252 | GCCG | AA | GCC | | | AAA | | | GGC | AAAAA | CGGC |
| 253 | GCCG | AAAA | GCC | | | AAA | | | GGC | AAA | CGGC |
| 254 | GCCG | AAA | GCC | | | AAA | | | GGC | AAAA | CGGC |
| 255 | GCCG | AA | GCC | A | GC | AAA | GC | | GGC | | CGGC |
| 256 | GCCG | | GCC | A | GC | AAA | GC | | GGC | AA | CGGC |
| 257 | GCCG | AA | GCC | | GC | AAA | GC | A | GGC | | CGGC |
| 258 | GCCG | | GCC | | GC | AAA | GC | A | GGC | AA | CGGC |
| 259 | GCCG | A | GCC | AA | GC | AAA | GC | | GGC | | CGGC |
| 260 | GCCG | | GCC | AA | GC | AAA | GC | | GGC | A | CGGC |
| 261 | GCCG | A | GCC | | GC | AAA | GC | AA | GGC | | CGGC |
| 262 | GCCG | | GCC | | GC | AAA | GC | AA | GGC | A | CGGC |
| 263 | GCCG | A | GCC | A | GC | AAA | GC | | GGC | A | CGGC |
| 264 | GCCG | A | GCC | | GC | AAA | GC | A | GGC | A | CGGC |
| 265 | GCCG | A | GCC | A | GC | AAA | GC | A | GGC | | CGGC |
| 266 | GCCG | | GCC | A | GC | AAA | GC | A | GGC | A | CGGC |
| 267 | GCCG | AAAAA | GC | | | AAA | | | GC | AAAA | CGGC |
| 268 | GCCG | AAAA | GC | | | AAA | | | GC | AAAAA | CGGC |

-continued

| SEQ ID NO | S1 | P1 | S2 | P3 | S3 | L | S3 | P4 | S2 | P2 | S1 |
|---|---|---|---|---|---|---|---|---|---|---|---|
| 269 | GCCG | AA | GC | A | GCC | AAA | GGC | | GC | | CGGC |
| 270 | GCCG | | GC | A | GCC | AAA | GGC | | GC | AA | CGGC |
| 271 | GCCG | AA | GC | | GCC | AAA | GGC | A | GC | | CGGC |
| 272 | GCCG | | GC | | GCC | AAA | GGC | A | GC | AA | CGGC |
| 273 | GCCG | A | GC | AA | GCC | AAA | GGC | | GC | | CGGC |
| 274 | GCCG | | GC | AA | GCC | AAA | GGC | | GC | A | CGGC |
| 275 | GCCG | A | GC | | GCC | AAA | GGC | AA | GC | | CGGC |
| 276 | GCCG | | GC | | GCC | AAA | GGC | AA | GC | A | CGGC |
| 277 | GCCG | A | GC | A | GCC | AAA | GGC | | GC | A | CGGC |
| 278 | GCCG | A | GC | | GCC | AAA | GGC | A | GC | A | CGGC |
| 279 | GCCG | A | GC | A | GCC | AAA | GGC | A | GC | | CGGC |
| 280 | GCCG | | GC | A | GCC | AAA | GGC | A | GC | A | CGGC |
| 281 | GCCG | AAAA | GC | A | GC | AAA | GC | | GC | | CGGC |
| 282 | GCCG | | GC | A | GC | AAA | GC | | GC | AAAA | CGGC |
| 283 | GCCG | AAAA | GC | | GC | AAA | GC | A | GC | | CGGC |
| 284 | GCCG | | GC | | GC | AAA | GC | A | GC | AAAA | CGGC |
| 285 | GCCG | A | GC | AAAA | GC | AAA | GC | | GC | | CGGC |
| 286 | GCCG | A | GC | | GC | AAA | GC | AAAA | GC | | CGGC |
| 287 | GCCG | | GC | AAAA | GC | AAA | GC | | GC | A | CGGC |
| 288 | GCCG | | GC | | GC | AAA | GC | AAAA | GC | A | CGGC |
| 289 | GCCG | AAA | GC | AA | GC | AAA | GC | | GC | | CGGC |
| 290 | GCCG | | GC | AA | GC | AAA | GC | | GC | AAA | CGGC |
| 291 | GCCG | AAA | GC | | GC | AAA | GC | AA | GC | | CGGC |
| 292 | GCCG | | GC | | GC | AAA | GC | AA | GC | AAA | CGGC |
| 293 | GCCG | AA | GC | AAA | GC | AAA | GC | | GC | | CGGC |
| 294 | GCCG | AA | GC | | GC | AAA | GC | AAA | GC | | CGGC |
| 295 | GCCG | | GC | AAA | GC | AAA | GC | | GC | AA | CGGC |
| 296 | GCCG | | GC | | GC | AAA | GC | AAA | GC | AA | CGGC |
| 297 | GCCG | AAA | GC | A | GC | AAA | GC | A | GC | | CGGC |
| 298 | GCCG | AAA | GC | | GC | AAA | GC | A | GC | A | CGGC |
| 299 | GCCG | AAA | GC | A | GC | AAA | GC | | GC | A | CGGC |
| 300 | GCCG | | GC | A | GC | AAA | GC | A | GC | AAA | CGGC |
| 301 | GCCG | A | GC | | GC | AAA | GC | A | GC | AAA | CGGC |
| 302 | GCCG | A | GC | A | GC | AAA | GC | | GC | AAA | CGGC |
| 303 | GCCG | A | GC | AAA | GC | AAA | GC | | GC | A | CGGC |
| 304 | GCCG | | GC | AAA | GC | AAA | GC | A | GC | A | CGGC |
| 305 | GCCG | A | GC | AAA | GC | AAA | GC | A | GC | | CGGC |
| 306 | GCCG | A | GC | | GC | AAA | GC | AAA | GC | A | CGGC |

-continued

| SEQ ID NO | S1 | P1 | S2 | P3 | S3 | L | S3 | P4 | S2 | P2 | S1 |
|---|---|---|---|---|---|---|---|---|---|---|---|
| 307 | GCCG | A | GC | A | GC | AAA | GC | AAA | GC | | CGGC |
| 308 | GCCG | | GC | A | GC | AAA | GC | AAA | GC | A | CGGC |
| 309 | GCCG | AA | GC | A | GC | AAA | GC | | GC | AA | CGGC |
| 310 | GCCG | AA | GC | | GC | AAA | GC | A | GC | AA | CGGC |
| 311 | GCCG | A | GC | AA | GC | AAA | GC | AA | GC | | CGGC |
| 312 | GCCG | | GC | AA | GC | AAA | GC | AA | GC | A | CGGC |
| 313 | GCCG | AA | GC | AA | GC | AAA | GC | | GC | A | CGGC |
| 314 | GCCG | AA | GC | | GC | AAA | GC | AA | GC | A | CGGC |
| 315 | GCCG | AA | GC | AA | GC | AAA | GC | A | GC | | CGGC |
| 316 | GCCG | | GC | AA | GC | AAA | GC | A | GC | AA | CGGC |
| 317 | GCCG | A | GC | AA | GC | AAA | GC | | GC | AA | CGGC |
| 318 | GCCG | A | GC | | GC | AAA | GC | AA | GC | AA | CGGC |
| 319 | GCCG | AA | GC | A | GC | AAA | GC | AA | GC | | CGGC |
| 320 | GCCG | | GC | A | GC | AAA | GC | AA | GC | AA | CGGC |
| 321 | GCCG | AA | GC | A | GC | AAA | GC | A | GC | A | CGGC |
| 322 | GCCG | A | GC | A | GC | AAA | GC | A | GC | AA | CGGC |
| 323 | GCCG | A | GC | AA | GC | AAA | GC | A | GC | A | CGGC |
| 324 | GCCG | A | GC | A | GC | AAA | GC | AA | GC | A | CGGC |

Example III

Example of Chip Based Selection of Aptamers

Figure 5:
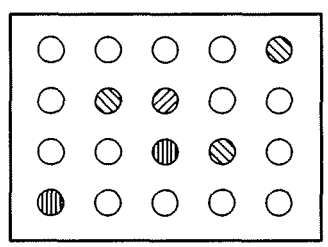
FIG. 5 depicts a chip having an exemplary selection and counterselection of aptamer geometries.

In an exemplary embodiment, following geometric enrichment and further enrichment, selection of aptamers is performed directly on a chip as shown in FIG. 5. Labeled analyte is passed across the microarray of aptamers for both wild type and variant. Those aptamers which are specific to only the wildtype are selected for further examination and characterization.

Example IV

Example of Combining Two Aptamers for Enhanced Performance

Figure 6:
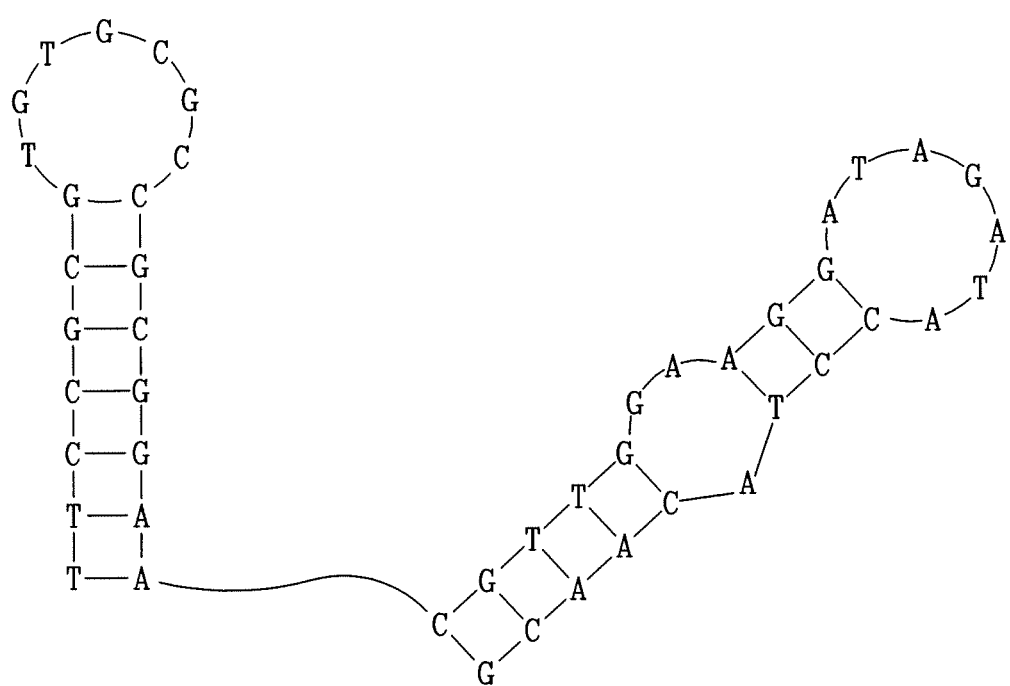
FIG. 6 depicts two specific aptamers combined cooperatively to achieve greater affinity.

In an exemplary embodiment, individual aptamers which have been independently specific for the target are combined together as shown in FIG. 6. In an exemplary embodiment, the linker is polyethylene glycol. In an exemplary embodiment, each possible geometrically enriched aptamer is placed in a pair with another geometrically enriched aptamer and placed in a microarray. As in Example III, wild type and variant analyte is passed across the microarray, allowing for selection and counter selection of the appropriate aptamer pair. Those aptamer pairs showing the highest affinity for the target and with no detectable affinity towards the variant are chosen.

Example V

Example of Chip Based Selection of Aptamers for gp120

In an exemplary embodiment, following geometric enrichment and further enrichment, selection of aptamers was performed directly on a chip: Aptamers hybridizations were performed on a TCAN 4800hs automated hybridization station according to the following protocol: 1) Denature aptamers with 30 s wash at 85° C. with 0.1% SDS in di H$_2$O, incubate at 85° C. for 30 s while shaking, wash at 85° C. for 30 s 2) Repeat with di H$_2$O 3) Block with 0.1% Tween in PBS buffer and 5 mM MgCl$_2$ at 23° C. by washing for 30 s, incubating/shaking for 30 s, and washing for 30 more seconds 4) Inject 100 μL of 1 to 10 μM protein (BSA, gp120) and hybridize for 30 min while shaking 5) Wash with 0.1% Tween in PBS buffer and 5 mM MgCl$_2$ at 23° C. for 10 s 6) Wash with PBS buffer and 5 mM MgCl$_2$ at 23° C. for 20 s 7) Dry and image on GenePix 4000B scanner.

Figure 7:
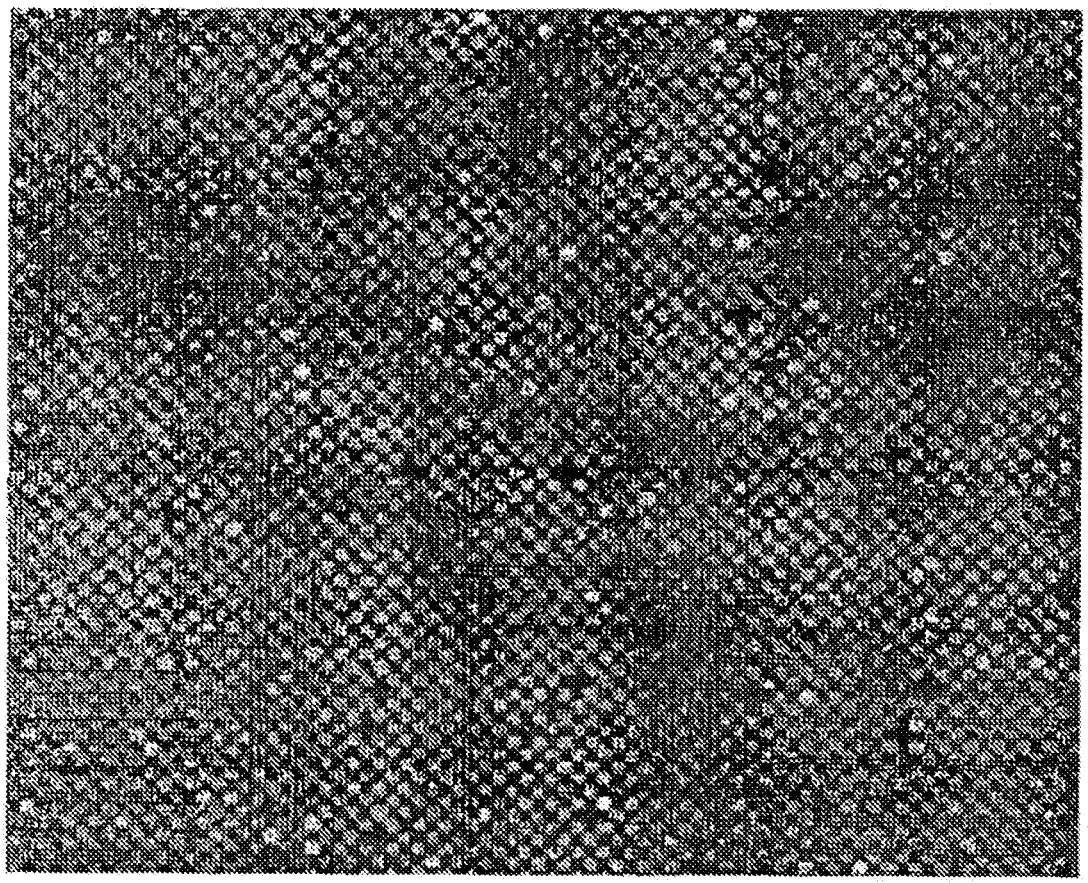
FIG. 7 illustrates an exemplary section of aptamer array following hybridization with 10 µM bovine serum albumin (BSA), in which aptamers having affinity for BSA appear as spots having a fluorescent intensity significantly above the background intensity.
Figure 8:
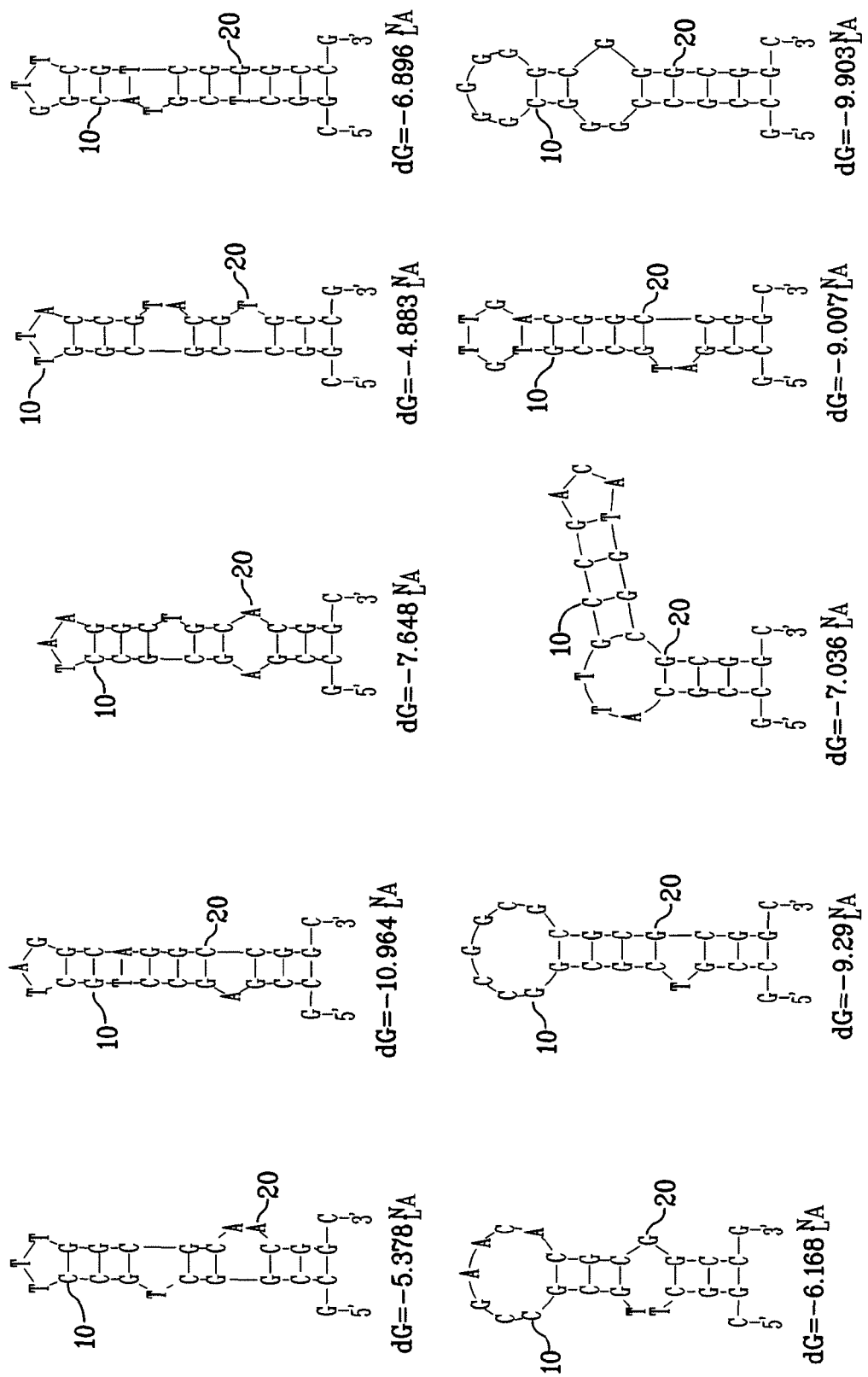
FIG. 8 depicts exemplary aptamer geometries and sequences selected for HIV gp120 using the claimed geometric selection protocol—it was discovered that none of the aptamers binding to HIV gp120 bound to BSA.

Alignment was performed using NimbleScan v2.2 software and aptamers were selected by exceeding the average fluorescence plus three standard deviations of aptamers containing 100% thymine in the variable loop regions. In order to be selected as an aptamer, 3 of the 4 replicates had to exceed this level of fluorescence (FIG. 7). Ten aptamers were selected for HIV gp120 (FIG. 8). The aptamers selected for HIV gp120 did not have the same geometries or content as the aptamers that were selected for BSA.

The examples set forth above are provided to give those of ordinary skill in the art with a complete disclosure and description of how to make and use the preferred embodiments of the present invention, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

1. Tuerk, C. and Gold, L. (1990) Systematic evolution of ligands by exponential enrichment: RNA ligands to bacteriophage T4 DNA polymerase. *Science,* 249, 505-510.
2. Gold, L. and Tuerk, C. (2004) U.S. Pat. No. 6,716,583.
3. West, J. A. A. and Satterfield, B. C. (2006) USA.
4. Mescalchin, A., Wunsche, W., Laufer, S. D., Grohmann, D., Restle, T. and Sczakiel, G. (2006) Specific binding of a hexanucleotide to HIV-1 reverse transcriptase: a novel class of bioactive molecules. *Nucleic Acids Res.*
5. Asai, R., Nishimura, S. I., Aita, T. and Takahashi, K. (2004) In Vitro Selection of DNA Aptamers on Chips Using a Method for Generating Point Mutations. *Chemical and Biosensors,* 37, 645-656.
6. Hirao, I., Spingola, M., Peabody, D. and Ellington, A. D. (1998) The limits of specificity: an experimental analysis with RNA aptamers to MS2 coat protein variants. *Mol Divers,* 4, 75-89.
7. Cerchia, L., Duconge, F., Pestourie, C., Boulay, J., Aissouni, Y., Gombert, K., Tavitian, B., de Franciscis, V. and Libri, D. (2005) Neutralizing aptamers from whole-cell SELEX inhibit the RET receptor tyrosine kinase. *PLoS Biol,* 3, e123.
8. Mannironi, C., Di Nardo, A., Fruscoloni, P. and Tocchini-Valentini, G. P. (1997) In vitro selection of dopamine RNA ligands. *Biochemistry,* 36, 9726-9734.
9. Boiziau, C., Dausse, E., Yurchenko, L. and Toulme, J. J. (1999) DNA aptamers selected against the HIV-1 trans-activation-responsive RNA element form RNA-DNA kissing complexes. *J Biol Chem,* 274, 12730-12737.
10. Rhodes, A., Deakin, A., Spaull, J., Coomber, B., Aitken, A., Life, P. and Rees, S. (2000) The generation and characterization of antagonist RNA aptamers to human oncostatin M. *J Biol Chem,* 275, 28555-28561.
11. Ruckman, J., Green, L. S., Beeson, J., Waugh, S., Gillette, W. L., Henninger, D. D., Claesson-Welsh, L. and Janjic, N. (1998) 2'-Fluoropyrimidine RNA-based aptamers to the 165-amino acid form of vascular endothelial growth factor (VEGF 165). Inhibition of receptor binding and VEGF-induced vascular permeability through interactions requiring the exon 7-encoded domain. *J Biol Chem,* 273, 20556-20567.
12. Pileur, F., Andreola, M. L., Dausse, E., Michel, J., Moreau, S., Yamada, H., Gaidamakov, S. A., Crouch, R. J., Toulme, J. J. and Cazenave, C. (2003) Selective inhibitory DNA aptamers of the human RNase H1. *Nucleic Acids Res,* 31, 5776-5788.
13. Tasset, D. M., Kubik, M. F. and Steiner, W. (1997) Oligonucleotide inhibitors of human thrombin that bind distinct epitopes. *J Mol Biol,* 272, 688-698.
14. Okazawa, A., Maeda, H., Fukusaki, E., Katakura, Y. and Kobayashi, A. (2000) In vitro selection of hematoporphyrin binding DNA aptamers. *Bioorg Med Chem Lett,* 10, 2653-2656.
15. Amarasinghe, A. K., MacDiamid, R., Adams, M. D. and Rio, D. C. (2001) An in vitro-selected RNA-binding site for the KH domain protein PSI acts as a splicing inhibitor element. *Rna,* 7, 1239-1253.
16. Vo, N. V., Oh, J. W. and Lai, M. M. (2003) Identification of RNA ligands that bind hepatitis C virus polymerase selectively and inhibit its RNA synthesis from the natural viral RNA templates. *Virology,* 307, 301-316.
17. Dang, C. and Jayasena, S. D. (1996) Oligonucleotide inhibitors of Taq DNA polymerase facilitate detection of low copy number targets by PCR. *J Mol Biol,* 264, 268-278.
18. Mendonsa, S. D. and Bowser, M. T. (2004) In vitro evolution of functional DNA using capillary electrophoresis. *J Am Chem Soc,* 126, 20-21.
19. Mendonsa, S. D. and Bowser, M. T. (2005) In vitro selection of aptamers with affinity for neuropeptide Y using capillary electrophoresis. *J Am Chem Soc,* 127, 9382-9383.
20. Bellecave, P., Andreola, M. L., Ventura, M., Tarrago-Litvak, L., Litvak, S. and Astier-Gin, T. (2003) Selection of DNA aptamers that bind the RNA-dependent RNA polymerase of hepatitis C virus and inhibit viral RNA synthesis in vitro. *Oligonucleotides,* 13, 455-463.
21. Daniels, D. A., Sohal, A. K., Rees, S. and Grisshammer, R. (2002) Generation of RNA aptamers to the G-protein-coupled receptor for neurotensin, NTS-1. *Anal Biochem,* 305, 214-226.
22. Surugiu-Warnmark, I., Warnmark, A., Toresson, G., Gustafsson, J. A. and Bulow, L. (2005) Selection of DNA aptamers against rat liver X receptors. *Biochem Biophys Res Commun,* 332, 512-517.
23. Schneider, D., Gold, L. and Platt, T. (1993) Selective enrichment of RNA species for tight binding to *Escherichia coli* rho factor. *Faseb J,* 7, 201-207.
24. Hirao, I., Madin, K., Endo, Y., Yokoyama, S, and Ellington, A. D. (2000) RNA aptamers that bind to and inhibit the ribosome-inactivating protein, pepocin. *J Biol Chem,* 275, 4943-4948.
25. Yang, Q., Goldstein, I. J., Mei, H. Y. and Engelke, D. R. (1998) DNA ligands that bind tightly and selectively to cellobiose. *Proc Natl Acad Sci USA,* 95, 5462-5467.
26. Wang, C., Zhang, M., Yang, G., Zhang, D., Ding, H., Wang, H., Fan, M., Shen, B. and Shao, N. (2003) Single-stranded DNA aptamers that bind differentiated but not parental cells: subtractive systematic evolution of ligands by exponential enrichment. *J Biotechnol,* 102, 15-22.

What is claimed:

1. A method, comprising:
geometrically enriching a plurality of aptamers of a given length or a range of aptamer lengths, wherein said geometric enrichment comprises formulating a set of possible aptamer geometries, wherein the aptamer geometries in the set share a common format defined by the number of stems, loops, and pockets present in the aptamer structure, and wherein the format comprises one or more stems, one or more loops, and one or more pockets, and:
  each loop in the common format has a size of no less than 3 nucleotides and no more than 21 nucleotides,
  each pocket in the common format has a size of no less than 1 nucleotide and no more than 8 nucleotides, and
  each stem in the common format has a size of no less than 2 nucleotides and no more than 7 nucleotides;
further enriching the set of possible aptamer geometries by formulating a library of aptamer sequences from the set of geometries, wherein the library is formulated by excluding sequences that do not satisfy one or more selected aptamer statistics relating to sequence(s) of stems, loops, and/or pockets, wherein the aptamer statistics are derived from data on pre-existing apatmers, and wherein the library comprises more than 1% of all possible geometries for a given aptamer length;
affixing at least one candidate aptamer from the library of aptamer sequences to a substrate.

2. The method of claim 1 wherein the library comprises more than 10% of all possible geometries for a given aptamer length.

3. The method of claim 1 in which the aptamer statistic relating to sequence comprises stem GC content, and the stem GC content in aptamer sequences in the library is greater than 50%.

4. The method of claim 2 in which the aptamer statistic relating to sequence comprises stem GC content, and the stem GC content in aptamer sequences in the library is greater than 50%.

5. The method of claim 1 wherein a plurality of candidate aptamers is affixed to the substrate to form a microarray.

6. The method of claim 1 wherein two or more candidate aptamers are linked directly or indirectly and then affixed to the substrate.

7. The method of claim 6 wherein a plurality of linked aptamers is affixed to the substrate to form a microarray.

8. The method of claim 4 wherein two or more candidate aptamers are linked directly or indirectly and then affixed to the substrate.

9. The method of claim 8 wherein a plurality of linked aptamers is affixed to the substrate to form a microarray.

10. The method of claim 1 wherein one or more candidate aptamers is linked with one or more ligands and then affixed to the substrate.

11. The method of claim 10 wherein a plurality of ligand-linked aptamers is affixed to the substrate to form a microarray.

12. The method of claim 4 wherein one or more candidate aptamers is linked with one or more ligands selected through other means and then affixed to the substrate.

13. The method of claim 12 wherein a plurality of ligand-linked aptamers is affixed to the substrate to form a microarray.

14. The method of claim 1 wherein the method additionally comprises:
  contacting the at least one candidate aptamer with at least one target; and assaying for binding between the at least one target and the at least one candidate aptamer.

15. The method of claim 14, wherein the assaying comprises monitoring a fluorescent signal related to binding between the at least one target and the at least one candidate aptamer.

16. The method of claim 15, comprising contacting the at least one candidate aptamer with a wild-type target and a variant target.

17. The method of claim 14, further comprising monitoring binding over time to determine binding kinetics of the at least one candidate aptamer.

18. The method of claim 14, further comprising monitoring binding over multiple concentrations of one or more candidate aptamers so as to determine aptamer affinities.

19. The method of claim 14, further comprising monitoring binding between the at least one target and one or more candidate aptamers to so as to determine the inhibition, the acceleration, or both of a process.

20. The method of claim 19, wherein the process is enzymatic in nature.

21. The method of claim 19, wherein binding is used to determine acceleration of a process.

22. The method of claim 21, wherein the process is enzymatic in nature.

23. The method of claim 16, wherein contrast between wild type and variant binding is used to select aptamers.

24. The method of claim 14, wherein a plurality of candidate aptamers is affixed to the substrate to form a microarray, and wherein binding over time is used to observe kinetics of individual aptamers.

25. The method of claim 14, wherein a plurality of candidate aptamers is affixed to the substrate to form a microarray, and wherein binding over multiple concentrations is used to determine aptamer affinities.

26. The method of claim 14, wherein a plurality of candidate aptamers is affixed to the substrate to form a microarray, and wherein binding is used to determine inhibition of a process.

27. The method of claim 26, wherein the process is enzymatic in nature.

28. The method of claim 14, wherein binding is used to determine acceleration of a process.

29. The method of claim 28, wherein the process is enzymatic in nature.

30. The method of claim 14, wherein a plurality of linked aptamers is affixed to the substrate to form a microarray, and wherein the assaying comprises monitoring binding to the microarray via fluorescence.

31. The method of claim 30, wherein contrast between wild type and variant binding is used to select linked aptamers.

32. The method of claim 14, wherein a plurality of linked aptamers is affixed to the substrate to form a microarray, and wherein binding over time is used to observe kinetics of individual linked aptamers.

33. The method of claim 14, wherein a plurality of linked aptamers is affixed to the substrate to form a microarray, and wherein binding over multiple concentrations is used to determine linked aptamer affinities.

34. The method of claim 14, wherein a plurality of linked aptamers is affixed to the substrate to form a microarray, and wherein binding is used to determine inhibition of a process.

35. The method of claim 34, wherein the process is enzymatic in nature.

36. The method of claim 14, wherein a plurality of linked aptamers is affixed to the substrate to form a microarray, and wherein binding is used to determine acceleration of a process.

37. The method of claim 36, wherein the process is enzymatic in nature.

38. The method of claim 14, wherein a plurality of linked aptamers is affixed to the substrate to form a microarray, and wherein the assaying comprises monitoring binding to the microarray via fluorescence.

39. The method of claim 38, wherein contrast between wild type and variant binding is used to select linked aptamers.

40. The method of claim 14, wherein a plurality of linked aptamers is affixed to the substrate to form a microarray, and wherein binding over time is used to observe kinetics of individual linked aptamers.

41. The method of claim 14, wherein a plurality of linked aptamers is affixed to the substrate to form a microarray, and wherein binding over multiple concentrations is used to determine linked aptamer affinities.

42. The method of claim 14, wherein a plurality of linked aptamers is affixed to the substrate to form a microarray, and wherein binding is used to determine inhibition of a process.

43. The method of claim 42, wherein the process is enzymatic in nature.

44. The method of claim 14, wherein a plurality of linked aptamers is affixed to the substrate to form a microarray, and wherein binding is used to determine acceleration of a process.

45. The method of claim 44, wherein the process is enzymatic in nature.

46. The method of claim 14, wherein a plurality of ligand-linked aptamers is affixed to the substrate to form a microarray, and wherein the assaying comprises monitoring binding to the microarray via fluorescence.

47. The method of claim 46, wherein contrast between wild type and variant binding is used to select ligand-linked aptamers.

48. The method of claim 14, wherein a plurality of ligand-linked aptamers is affixed to the substrate to form a microarray, and wherein binding over time is used to observe kinetics of individual ligand-linked aptamers.

49. The method of claim 14, wherein a plurality of ligand-linked aptamers is affixed to the substrate to form a microarray, and wherein binding over multiple concentrations is used to determine ligand-linked aptamer affinities.

50. The method of claim 14, wherein a plurality of ligand-linked aptamers is affixed to the substrate to form a microarray, and wherein binding is used to determine inhibition of a process.

51. The method of claim 50, wherein the process is enzymatic in nature.

52. The method of claim 14, wherein a plurality of ligand-linked aptamers is affixed to the substrate to form a microarray, and wherein binding is used to determine acceleration of a process.

53. The method of claim 52, wherein the process is enzymatic in nature.

54. The method of claim 14, wherein a plurality of ligand-linked aptamers is affixed to the substrate to form a microarray, and wherein the assaying comprises monitoring binding to the microarray via fluorescence.

55. The method of claim 54, wherein contrast between wild type and variant binding is used to select ligand-linked aptamers.

56. The method of claim 14, wherein a plurality of ligand-linked aptamers is affixed to the substrate to form a microarray, and wherein binding over time is used to observe kinetics of individual ligand-linked aptamers.

57. The method of claim 14, wherein a plurality of ligand-linked aptamers is affixed to the substrate to form a microarray, and wherein binding over multiple concentrations is used to determine ligand-linked aptamer affinities.

58. The method of claim 14, wherein a plurality of ligand-linked aptamers is affixed to the substrate to form a microarray, and wherein binding is used to determine inhibition of a process.

59. The method of claim 58, wherein the process is enzymatic in nature.

60. The method of claim 14, wherein a plurality of ligand-linked aptamers is affixed to the substrate to form a microarray, and wherein binding is used to determine acceleration of a process.

61. The method of claim 60, wherein the process is enzymatic in nature.

* * * * *